United States Patent
Kubo et al.

(10) Patent No.: US 10,172,564 B2
(45) Date of Patent: Jan. 8, 2019

(54) APPARATUS, COMPUTER-READABLE MEDIUM, AND METHOD FOR DETECTING BIOLOGICAL DATA OF TARGET PATIENT FROM ATTACHABLE SENSOR ATTACHED TO TARGET PATIENT

(71) Applicant: OLYMPUS CORPORATION, Tokyo (JP)

(72) Inventors: Mitsunori Kubo, Tokyo (JP); Nobuyuki Watanabe, Tokyo (JP); Takatsugu Konno, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/832,409

(22) Filed: Dec. 5, 2017

(65) Prior Publication Data
US 2018/0140254 A1 May 24, 2018

Related U.S. Application Data

(63) Continuation of application No. PCT/JP2016/084846, filed on Nov. 24, 2016.

(51) Int. Cl.
*A61B 5/00* (2006.01)
*A61B 5/11* (2006.01)
(Continued)

(52) U.S. Cl.
CPC .......... *A61B 5/7221* (2013.01); *A61B 5/1118* (2013.01); *A61B 5/681* (2013.01);
(Continued)

(58) Field of Classification Search
CPC ...... G16H 10/60; G16H 40/63; A61B 5/7221; A61B 5/1118; A61B 5/6803; A61B 5/681; A61B 5/686; A61B 5/7203; A61B 5/7282
See application file for complete search history.

(56) References Cited

U.S. PATENT DOCUMENTS 3,835,837 A * 9/1974 Peek ...................... A61B 5/024
600/479
3,882,481 A 5/1975 Turner
(Continued)

FOREIGN PATENT DOCUMENTS

JP H09-113311 A 5/1997
JP 2002-049979 A 2/2002
(Continued)

OTHER PUBLICATIONS

PCT/ISA/210 (PCT/JP2016/084845), dated Jan. 31, 2017.
(Continued)

*Primary Examiner* — Sean P Dougherty
(74) *Attorney, Agent, or Firm* — Greer, Burns & Crain, Ltd.

(57) ABSTRACT

A apparatus for detecting a biological data of a target patient from an attachable sensor attached to the target patient includes a circuit and a storage that stores therein a first correspondence relationship between a state of a battery included in the sensor and a measurement error of the sensor. The circuit obtains the biological data and battery data indicating the state of the battery, the obtained biological data and the obtained battery data being collected by the sensor, and generates corrected biological data by correcting the biological data according to the battery data, wherein the generating of the corrected biological data includes generating correction data that depends on the battery data by referring to the storage that stores the first correspondence relationship, and generating the corrected biological data by correcting the biological data using the correction data.

19 Claims, 26 Drawing Sheets

(51) Int. Cl.
  *G16H 10/60* (2018.01)
  *G16H 40/63* (2018.01)

(52) U.S. Cl.
  CPC ............ *A61B 5/6803* (2013.01); *A61B 5/686* (2013.01); *A61B 5/7203* (2013.01); *A61B 5/7282* (2013.01); *G16H 10/60* (2018.01); *G16H 40/63* (2018.01); *A61B 2560/0214* (2013.01); *A61B 2560/0276* (2013.01); *A61B 2562/0219* (2013.01); *A61B 2562/0271* (2013.01)

(56) References Cited

U.S. PATENT DOCUMENTS

| | | | |
|---|---|---|---|
| 5,522,662 A * | 6/1996 | Shiokawa | G01J 5/0022 374/130 |
| 6,191,557 B1 * | 2/2001 | Gray | G01R 31/3682 320/132 |
| 6,561,978 B1 | 5/2003 | Conn et al. | |
| 6,996,427 B2 | 2/2006 | Ali et al. | |
| 8,467,726 B2 | 6/2013 | Shirakata et al. | |
| 8,512,246 B2 * | 8/2013 | Reggiardo | A61B 5/0002 340/539.1 |
| 9,901,307 B2 | 2/2018 | Kamath et al. | |
| 2004/0242972 A1 | 12/2004 | Adak et al. | |
| 2007/0159321 A1 | 7/2007 | Ogata et al. | |
| 2008/0054847 A1 * | 3/2008 | Elias | G01R 31/3627 320/130 |
| 2008/0092638 A1 | 4/2008 | Brenneman et al. | |
| 2008/0243021 A1 * | 10/2008 | Causevic | A61B 5/0002 600/544 |
| 2009/0036751 A1 | 2/2009 | Lutze et al. | |
| 2009/0058635 A1 | 3/2009 | LaLonde et al. | |
| 2009/0058636 A1 | 3/2009 | Gaskill et al. | |
| 2009/0062887 A1 | 3/2009 | Mass et al. | |
| 2009/0063187 A1 | 3/2009 | Johnson et al. | |
| 2009/0063193 A1 | 3/2009 | Barton et al. | |
| 2010/0010322 A1 | 1/2010 | Brady | |
| 2010/0152549 A1 | 6/2010 | Tamura | |
| 2010/0185101 A1 | 7/2010 | Sakai et al. | |
| 2010/0292544 A1 | 11/2010 | Sherman et al. | |
| 2011/0066009 A1 | 3/2011 | Moon et al. | |
| 2011/0098540 A1 | 4/2011 | Tanishima et al. | |
| 2011/0190646 A1 | 8/2011 | Kato et al. | |
| 2011/0205826 A1 | 8/2011 | Kuroda | |
| 2011/0273287 A1 | 11/2011 | LaLonde et al. | |
| 2011/0319734 A1 | 12/2011 | Gottlieb et al. | |
| 2011/0320166 A1 | 12/2011 | Luo et al. | |
| 2012/0051519 A1 | 3/2012 | Abe | |
| 2012/0092157 A1 | 4/2012 | Tran | |
| 2012/0095358 A1 | 4/2012 | Matsunaga et al. | |
| 2012/0157801 A1 | 6/2012 | Hoss et al. | |
| 2012/0165617 A1 | 6/2012 | Vesto et al. | |
| 2012/0262298 A1 | 10/2012 | Bohm et al. | |
| 2012/0265035 A1 | 10/2012 | Bohm et al. | |
| 2012/0265036 A1 | 10/2012 | Estes et al. | |
| 2012/0265037 A1 | 10/2012 | Bohm et al. | |
| 2012/0265549 A1 | 10/2012 | Virolainen | |
| 2013/0131465 A1 | 5/2013 | Yamamoto et al. | |
| 2013/0147622 A1 | 6/2013 | LaLonde et al. | |
| 2013/0154851 A1 | 6/2013 | Gaskill et al. | |
| 2013/0310896 A1 | 11/2013 | Mass | |
| 2013/0328572 A1 | 12/2013 | Wang et al. | |
| 2014/0000338 A1 | 1/2014 | Luo et al. | |
| 2014/0062718 A1 | 3/2014 | LaLonde et al. | |
| 2014/0114153 A1 | 4/2014 | Bohm et al. | |
| 2014/0114156 A1 | 4/2014 | Bohm et al. | |
| 2014/0125477 A1 | 5/2014 | Kasuya et al. | |
| 2014/0257073 A1 * | 9/2014 | Machon | A61B 5/6803 600/383 |
| 2014/0320307 A1 * | 10/2014 | Matsuno | A61B 5/0002 340/870.07 |
| 2014/0335490 A1 | 11/2014 | Baarman et al. | |
| 2015/0098309 A1 | 4/2015 | Adams et al. | |
| 2015/0130613 A1 | 5/2015 | Fullam | |
| 2015/0164387 A1 | 6/2015 | Varsavsky et al. | |
| 2015/0206408 A1 | 7/2015 | LaLonde et al. | |
| 2015/0316559 A1 | 11/2015 | Luo et al. | |
| 2016/0018246 A1 | 1/2016 | Bohm et al. | |
| 2016/0051154 A1 | 2/2016 | Iwawaki | |
| 2016/0058313 A1 | 3/2016 | Sato | |
| 2016/0073941 A1 | 3/2016 | Bohm et al. | |
| 2016/0077547 A1 | 3/2016 | Aimone et al. | |
| 2016/0157758 A1 | 6/2016 | Bohm et al. | |
| 2016/0174903 A1 | 6/2016 | Cutaia | |
| 2016/0198986 A1 | 7/2016 | Bohm et al. | |
| 2016/0278645 A1 | 9/2016 | Yoon | |
| 2016/0328991 A1 | 11/2016 | Simpson et al. | |
| 2016/0354033 A1 | 12/2016 | Ouchi et al. | |
| 2017/0010666 A1 | 1/2017 | Tanaka et al. | |
| 2017/0026814 A1 | 1/2017 | Naiki et al. | |
| 2017/0071541 A1 | 3/2017 | An | |
| 2017/0172424 A1 | 6/2017 | Eggers et al. | |
| 2018/0014742 A1 | 1/2018 | Iwawaki | |
| 2018/0017631 A1 * | 1/2018 | Kudo | G01R 31/36 |
| 2018/0045788 A1 * | 2/2018 | Kawai | G01R 31/3651 |
| 2018/0104410 A1 | 4/2018 | Gautham et al. | |

FOREIGN PATENT DOCUMENTS

| | | |
|---|---|---|
| JP | 2002-078211 A | 3/2002 |
| JP | 2002-224053 A | 8/2002 |
| JP | 2004216125 A | 8/2004 |
| JP | 2005-342134 A | 12/2005 |
| JP | 2006-238971 A | 9/2006 |
| JP | 2006-247386 A | 9/2006 |
| JP | 2009-045179 A | 3/2009 |
| JP | 2009-525089 A | 7/2009 |
| JP | 2010-517618 A | 5/2010 |
| JP | 2010-148718 A | 7/2010 |
| JP | 2010-162282 A | 7/2010 |
| JP | 2011-502369 A | 1/2011 |
| JP | 2011-104341 A | 6/2011 |
| JP | 2011-170943 A | 9/2011 |
| JP | 2012-045373 A | 3/2012 |
| JP | 2012-050620 A | 3/2012 |
| JP | 2012-139492 A | 7/2012 |
| JP | 2012-531948 A | 12/2012 |
| JP | 2013-027550 A | 2/2013 |
| JP | 2013-534439 A | 9/2013 |
| JP | 2014-094085 A | 5/2014 |
| JP | 2014-514093 A | 6/2014 |
| JP | 5576234 62 | 8/2014 |
| JP | 2015-154884 A | 8/2015 |
| JP | 2015-162734 A | 9/2015 |
| JP | 2015-177899 A | 10/2015 |
| JP | 2015-203926 A | 11/2015 |
| JP | 2016-043041 A | 4/2016 |
| JP | 2016-120065 A | 7/2016 |
| JP | 2016-137296 A | 8/2016 |
| JP | 2016-146954 A | 8/2016 |
| JP | 2016-158200 A | 9/2016 |
| WO | 9709923 A1 | 3/1997 |
| WO | WO 2006/046648 A1 | 5/2006 |
| WO | WO 2007/087840 A1 | 8/2007 |
| WO | WO 2008/097411 A1 | 8/2008 |
| WO | WO 2008/136050 A1 | 11/2008 |
| WO | WO 2009/032134 A2 | 3/2009 |
| WO | WO 2011/002694 A1 | 1/2011 |
| WO | WO 2011/163303 A2 | 12/2011 |
| WO | WO 2012/142502 A2 | 10/2012 |
| WO | WO 2013/161075 A1 | 10/2013 |
| WO | WO 2015/066430 A1 | 5/2015 |
| WO | 2016127130 A1 | 8/2016 |

OTHER PUBLICATIONS

Written Opinion of the ISA of PCT/JP2016/084845, dated Jan. 31, 2017 (with partial English translation).
PCT/ISA/210 (PCT/JP2016/084846), dated Feb. 21, 2017.
Written Opinion of the ISA of PCT/JP2016/084846, dated Feb. 21, 2017 (with partial English translation).

(56) References Cited

OTHER PUBLICATIONS

PCT/ISA/210 (PCT/JP2016/084847), dated Feb. 28, 2017.
Written Opinion of the ISA of PCT/JP2016/084847, dated Feb. 28, 2017 (with partial English translation).
PCT/ISA/210 (PCT/JP2016/084848), dated Feb. 21, 2017.
Written Opinion of the ISA of PCT/JP2016/084848, dated Feb. 21, 2017 (with partial English translation).
PCT/ISA/210 (PCT/JP2016/084849), dated Dec. 20, 2016.
Written Opinion of the ISA of PCT/JP2016/084849, dated Dec. 20, 2016 (with partial English translation).
U.S. Appl. No. 15/833,714, filed Dec. 6, 2017.
U.S. Appl. No. 15/832,927, filed Dec. 6, 2017.
U.S. Appl. No. 15/833,005, filed Dec. 6, 2017.
U.S. Appl. No. 15/832,332, filed Dec. 5, 2017.
FAI Pre-interview communication issued in corresponding U.S. Appl. No. 15/832,927, dated Mar. 22, 2018.
FAI pre-interview communication issued in corresponding U.S. Appl. No. 15/833,005, dated Apr. 5, 2018.
Hao et al; "Physiological Measurement"; vol. 29, pp. 1-59; 2008.
FAI Pre-Interview Communication issued in corresponding U.S. Appl. No. 15/833,714 dated May 2, 2018.
FAI Office Action Summary issued in U.S. Appl. No. 15/832,927 dated May 23, 2018.
FAI Office Action Summary issued in U.S. Appl. No. 15/833,005 dated Jun. 14, 2018.
FAI Pre-interview Communication issued in corresponding U.S. Appl. No. 15/832,332, dated Sep. 5, 2018.
FAI Office action summary issued in corresponding U.S. Appl. No. 15/833,714, dated Sep. 10, 2018.
Final Office Action issued in co-pending U.S. Appl. No. 15/832,927, dated Oct. 10, 2018.
Otto et al. "System Architecture of a Wireless Body Area Sensor Network for Ubiquitous Health Monitoring", Journal of Mobile Multimedia vol. 1 No. 4:307-326 (Year 2006).

\* cited by examiner

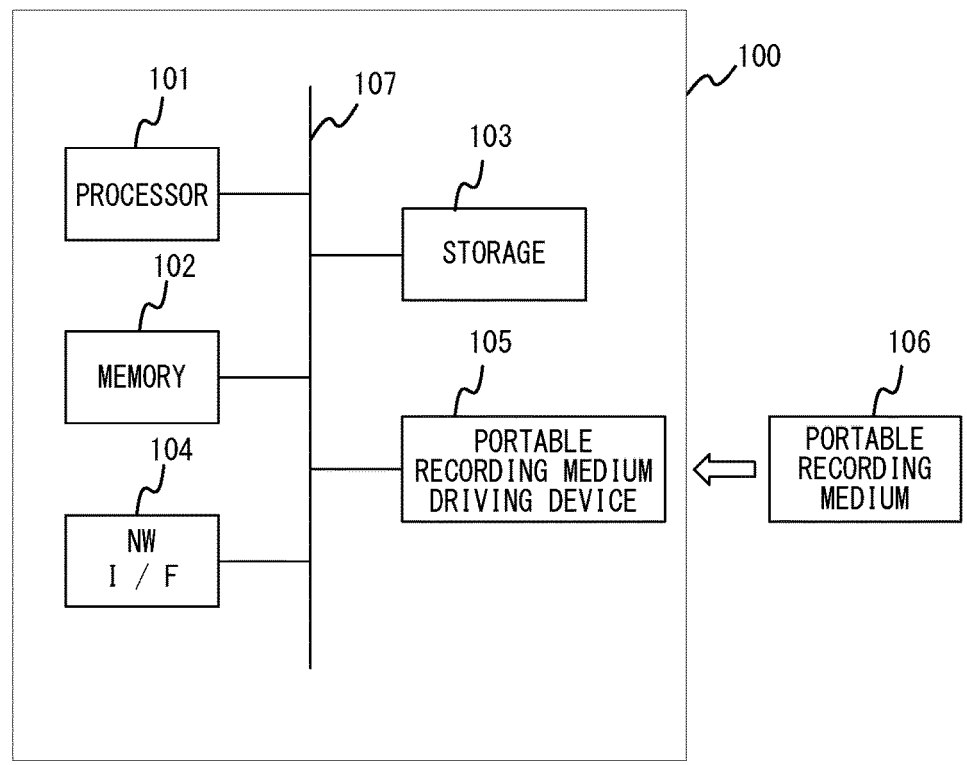
F I G. 3

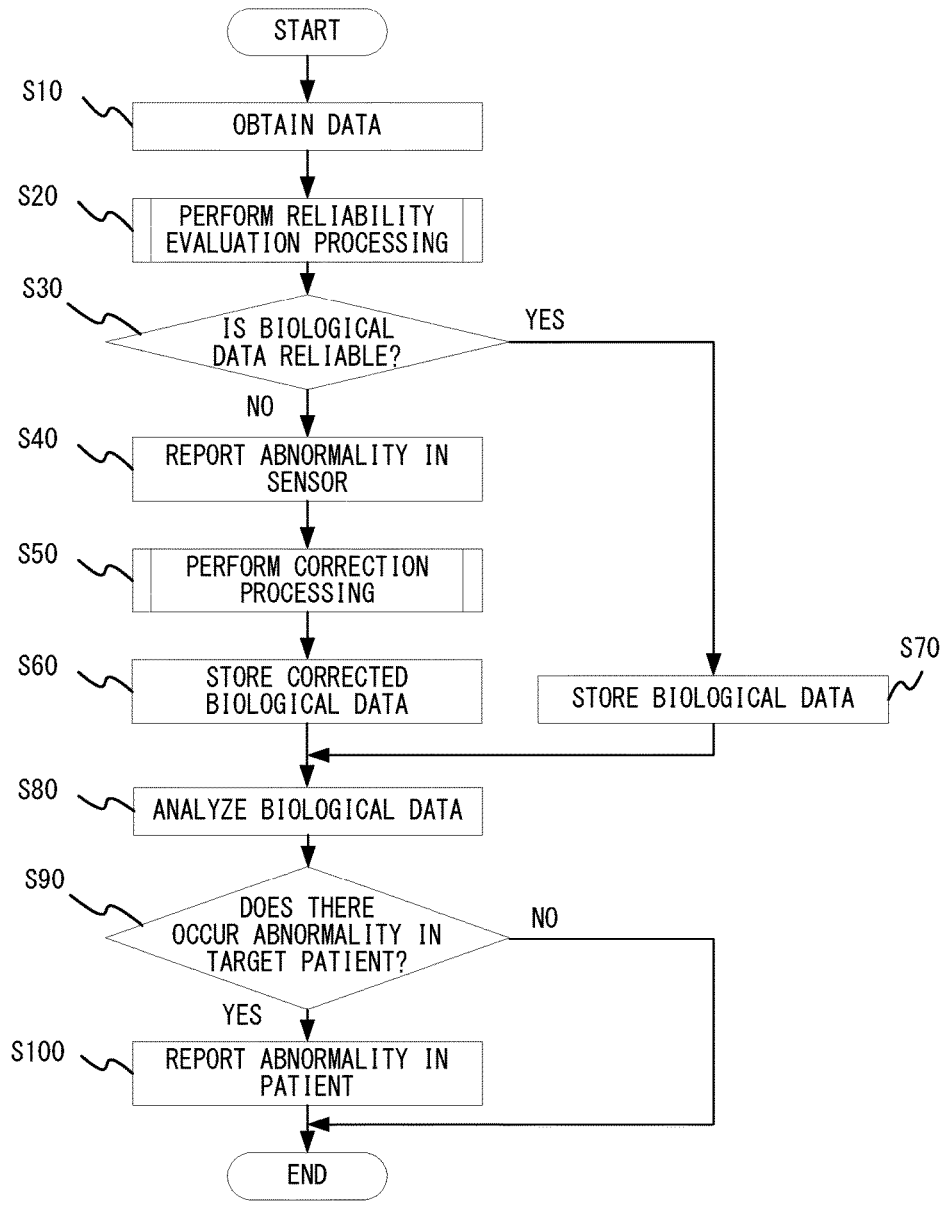
F I G. 4

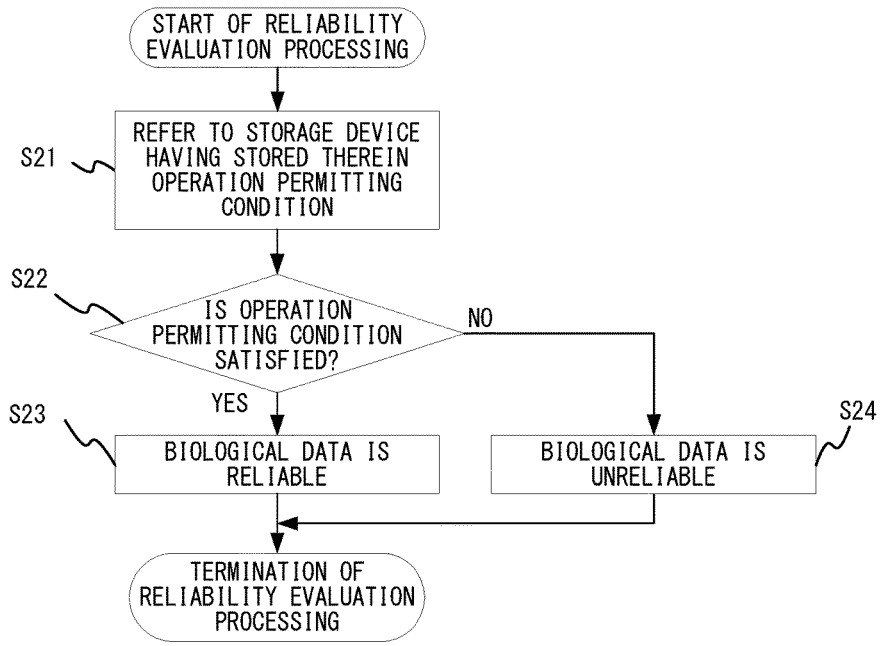
F I G. 5

| | | |
|---|---|---|
| POWER SUPPLY VOLTAGE | 5V±10% | |
| TEMPERATURE | 5°C TO 55°C | |
| CONTINUOUS USAGE TIME | 96 HOURS | |

MEASUREMENT ERROR (BLOOD PRESSURE)

MEASUREMENT ERROR (PULSE)

MEASUREMENT ERROR (BODY TEMPERATURE)

| | |
|---|---|
| POWER SUPPLY VOLTAGE | $\Delta V \times 10\%$ |
| TEMPERATURE | $\Delta Tc \times 20\%$ |
| CONTINUOUS USAGE TIME | $-\Delta t \times 3\%$ |

$\Delta V$ : DIFFERENCE BETWEEN POWER SUPPLY VOLTAGE OF SENSOR AND PERMITTED POWER SUPPLY VOLTAGE
("+" WHEN POWER SUPPLY VOLTAGE OF SENSOR > PERMITTED POWER SUPPLY VOLTAGE)

$\Delta Tc$ : DIFFERENCE BETWEEN TEMPERATURE OF SENSOR AND OPERATION PERMITTING TEMPERATURE
("+" WHEN TEMPERATURE OF SENSOR > OPERATION PERMITTING TEMPERATURE)

$\Delta t$ : DIFFERENCE BETWEEN CONTINUOUS USAGE TIME OF SENSOR AND PERMITTED CONTINUOUS USAGE TIME
("+" WHEN CONTINUOUS USAGE TIME OF SENSOR > PERMITTED CONTINUOUS USAGE TIME)

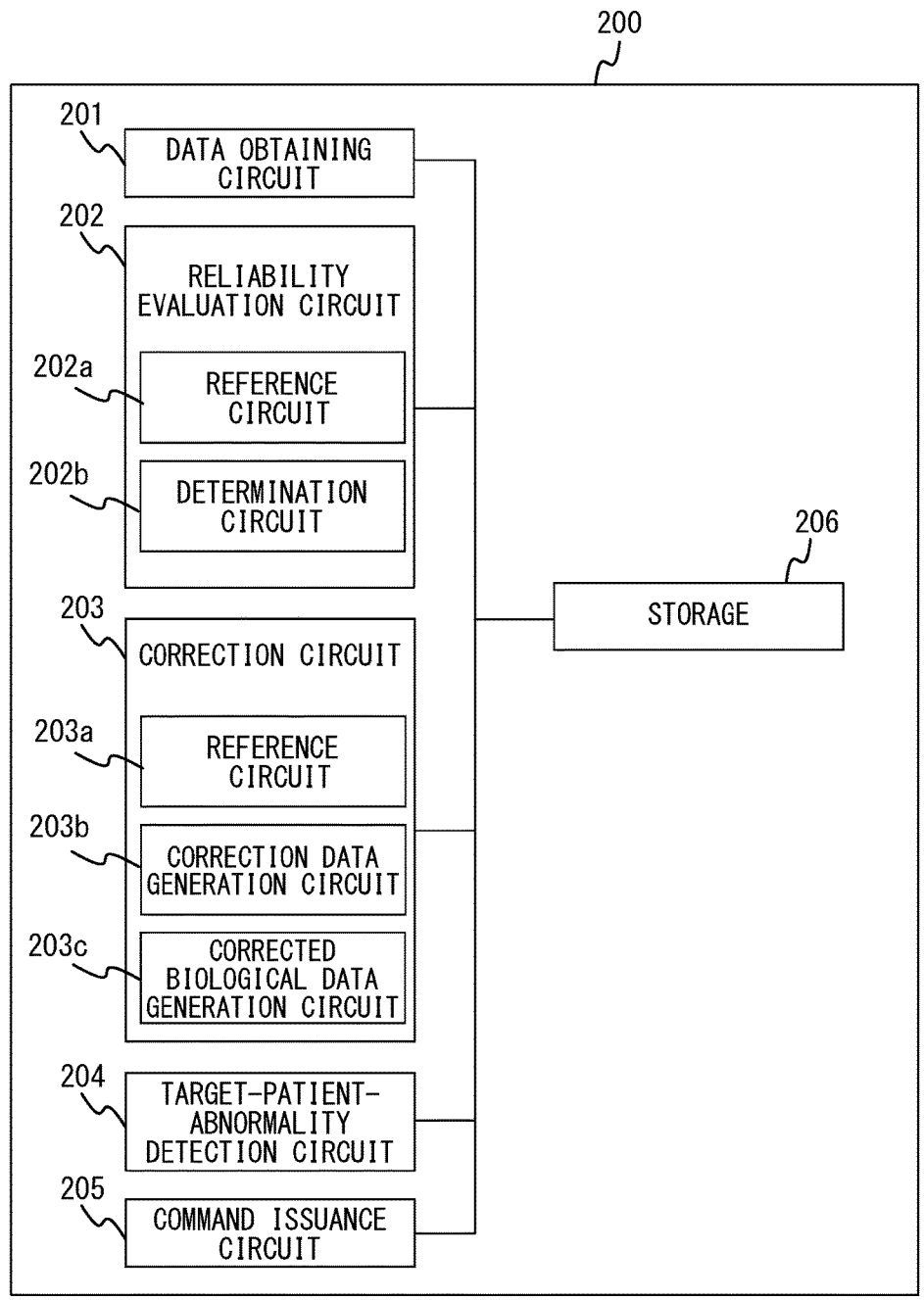
F I G. 9

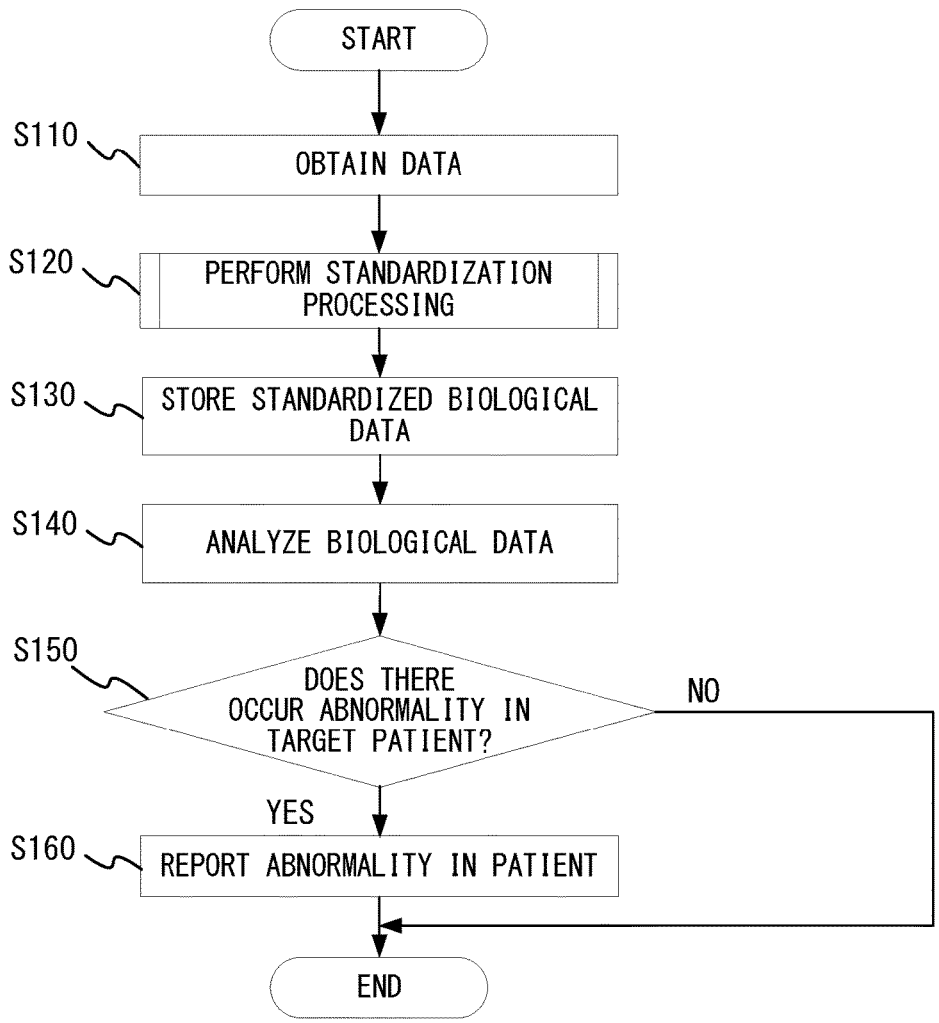
F I G. 1 0

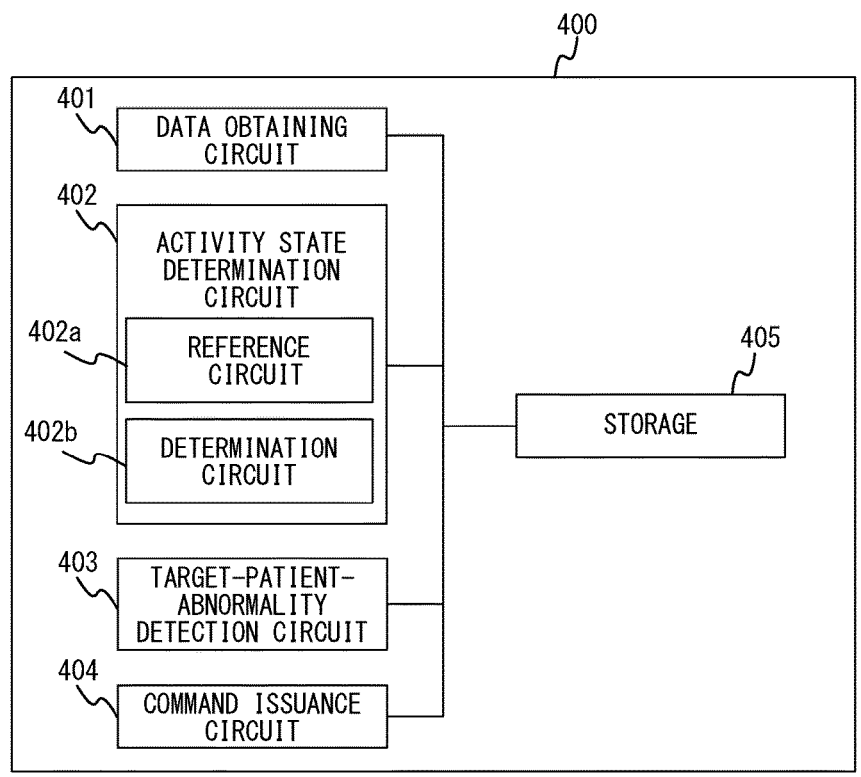
F I G. 1 7

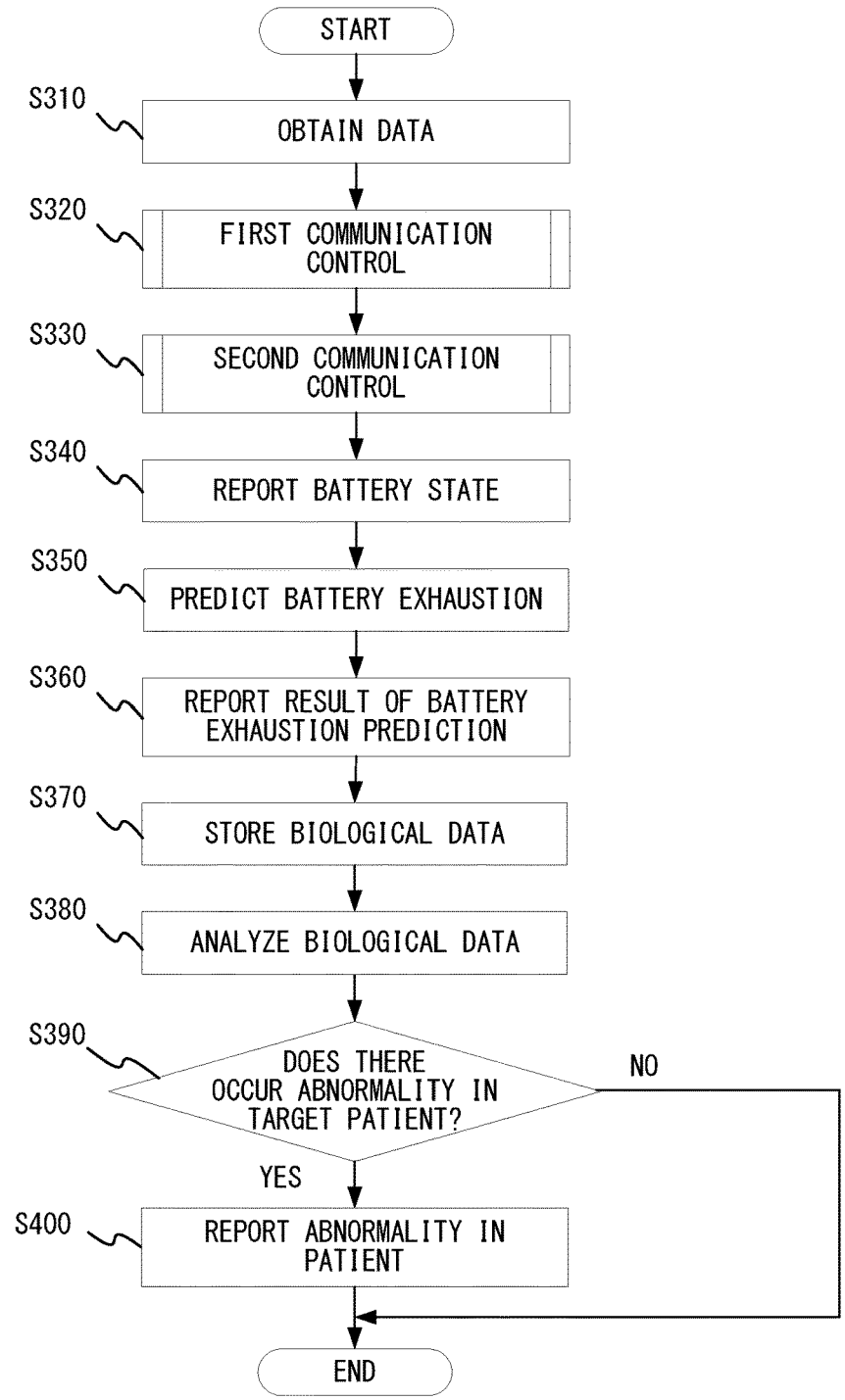
F I G. 1 8

| POWER SUPPLY VOLTAGE | RECOMMENDED COMMUNICATION INTERVAL | RECOMMENDED COMMUNICATION METHOD |
|---|---|---|
| ≧ 4.5V | 60s | WiFi |
| ≧ 4V and < 4.5V | 300s | WiFi |
| < 4V | − | NFC |

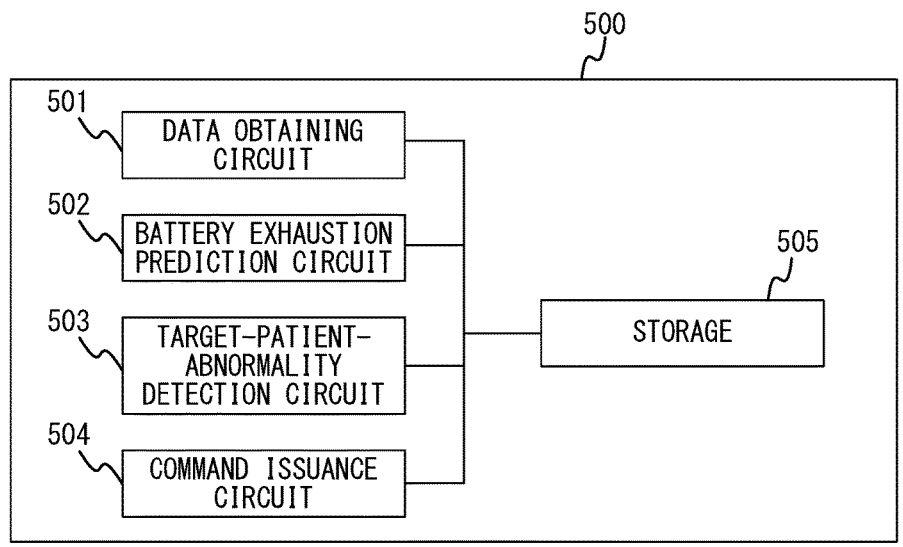
F I G. 2 2

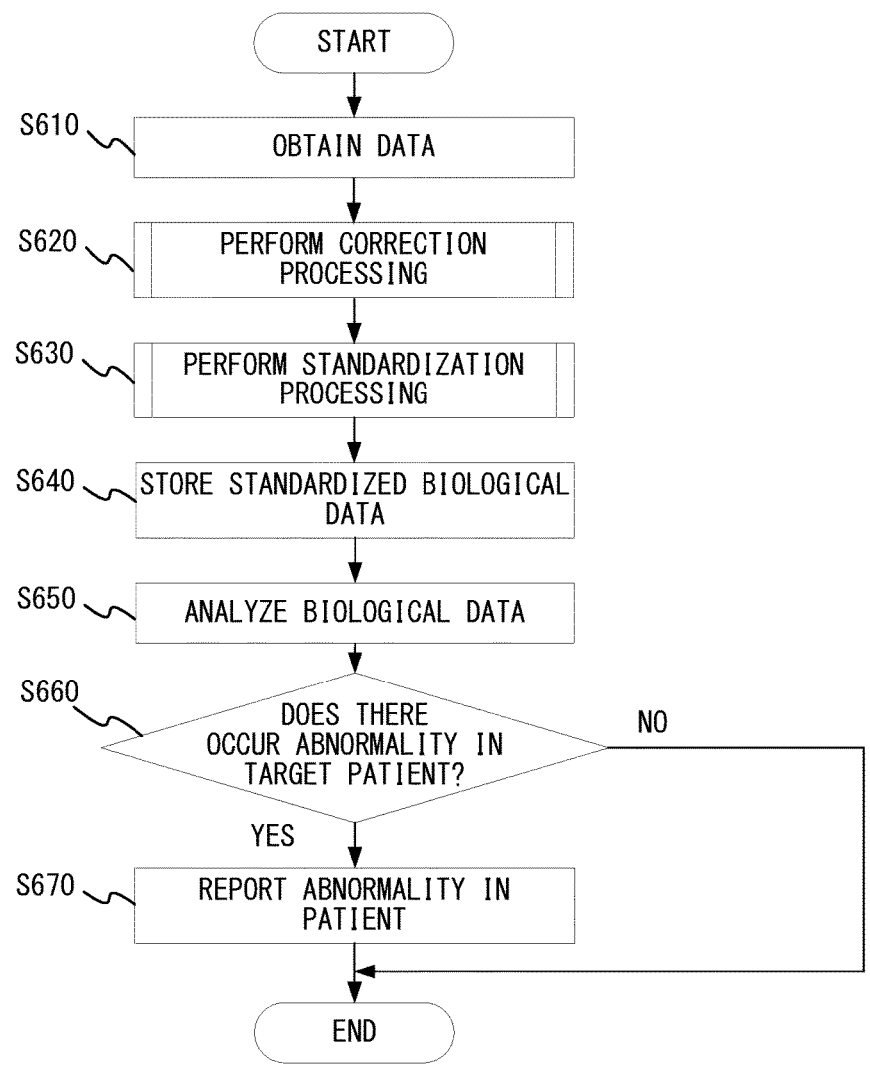
F I G. 2 5

APPARATUS, COMPUTER-READABLE MEDIUM, AND METHOD FOR DETECTING BIOLOGICAL DATA OF TARGET PATIENT FROM ATTACHABLE SENSOR ATTACHED TO TARGET PATIENT

CROSS-REFERENCE TO RELATED APPLICATIONS

This application is a Continuation application of PCT Application No. PCT/JP2016/084846, filed Nov. 24, 2016, the entire contents of all of which are incorporated herein by reference.

TECHNICAL FIELD

The present invention relates to an apparatus, a computer-readable medium, and a method for detecting a biological data of a target patient from an attachable sensor attached to the target patient.

RELATED ART

An information processing system is known that analyzes data (hereinafter referred to as biological data) indicating a physiological indicator of a patient for the purpose of being used in the treatment or prevention of disease.

Biological data of a patient has been obtained exclusively in medical institutions in the past, but in recent years, the development of a wearable sensor has made it possible to obtain biological data from a patient who lives their everyday life outside of a medical institution. For example, Patent Document 1 discloses a patient preventive health system that processes data received from a wearable sensor.

Patent Document 1: Japanese Laid-open Patent Publication No. 2012-139492

SUMMARY

An apparatus according to an aspect of the present invention is apparatus for detecting a biological data of a target patient from an attachable sensor attached to the target patient. The apparatus includes: a circuit; and a storage that stores therein a first correspondence relationship between a state of a battery included in the sensor and a measurement error of the sensor, wherein the circuit is configured to obtain the biological data and battery data indicating the state of the battery, the obtained biological data and the obtained battery data being collected by the sensor, and to generate corrected biological data by correcting the biological data according to the battery data, wherein the generating of the corrected biological data includes generating correction data that depends on the battery data by referring to the storage that stores the first correspondence relationship, and generating the corrected biological data by correcting the biological data using the correction data.

A computer-readable medium according to an aspect of the present invention is a non-transitory computer-readable medium having recorded therein a program for causing a computer to perform a process for detecting a biological data of a target patient from an attachable sensor attached to the target patient, the process including: obtaining the biological data and battery data indicating a state of a battery included in the sensor, the obtained biological data and the obtained battery data being collected by the sensor; and generating corrected biological data by correcting the biological data according to the battery data, wherein the generating of the corrected biological data includes generating correction data that depends on the battery data by referring to a storage that stores a first correspondence relationship between the state of the battery and a measurement error of the sensor, and generating the corrected biological data by correcting the biological data using the correction data.

A method according to an aspect of the present invention is a method for detecting a biological data of a target patient from an attachable sensor attached to the target patient. The method includes: obtaining the biological data and battery data indicating a state of a battery included in the sensor, the obtained biological data and the obtained battery data being collected by the sensor; and generating corrected biological data by correcting the biological data according to the battery data, wherein the generating of the corrected biological data includes generating correction data that depends on the battery data by referring to a storage that stores a first correspondence relationship between the state of the battery and a measurement error of the sensor, and generating the corrected biological data by correcting the biological data using the correction data.

BRIEF DESCRIPTION OF DRAWINGS

The present invention will be more apparent from the following detailed description when the accompanying drawings are referenced.

FIG. 3 illustrates a hardware configuration of a biological data processing apparatus 100;

FIG. 4 illustrates an example of a flowchart of data processing according to a first embodiment;

FIG. 5 illustrates an example of a flowchart of reliability evaluation processing;

FIG. 6 illustrates an example of information S1 on an operation permitting condition that is stored in a storage device 103;

FIG. 8 illustrates an example of information S2 on a correspondence relationship between a state of a sensor and a measurement error of the sensor that is stored in the storage 103;

FIG. 9 illustrates a hardware configuration of a biological data processing apparatus 200 according to a modification;

FIG. 10 is an example of a flowchart of data processing according to a second embodiment;

FIG. 17 illustrates a hardware configuration of a biological data processing apparatus 400 according to yet another modification;

FIG. 18 illustrates an example of a flowchart of data processing according to a fourth embodiment;

FIG. 22 illustrates a hardware configuration of a biological data processing apparatus 500 according to yet another modification;

FIG. 25 is another modification of the flowchart of the data processing illustrated in FIG. 23.

DESCRIPTION OF EMBODIMENTS

The usage of an attachable sensor, such as a wearable sensor, makes it possible to obtain biological data of a patient continually and routinely. This makes it possible to know a health condition of a patient earlier, so it is expected to be applied to the early treatment or prevention of disease.

On the other hand, attachable sensors are quite different from biological sensors (hereinafter referred to as bedside sensors) that have been conventionally used at bedside in, for example, medical institutions. For example, the attachable sensors are used under various circumstances in an everyday life of a patient, which is different from the bedside sensors that are used under specific controlled circumstances. Further, the attachable sensors obtain biological data from a patient (such as a patient who is moving or sleeping) in various activity states, which is different from the bedside sensors that obtain biological data from a patient at rest. Further, the attachable sensors use a battery as a power source, which is different from bedside sensors, which are used indoors, for example, inside a medical institution in which they can be stably supplied with power.

Due to the differences described above, the usage of an attachable sensor may cause unique problems that are different from problems of the past. Thus, a new technology that uses an attachable sensor effectively in the healthcare field for the treatment or prevention of disease is desired to be developed.

In light of the problem described above, embodiments of the present invention will now be described.

Figure 1:
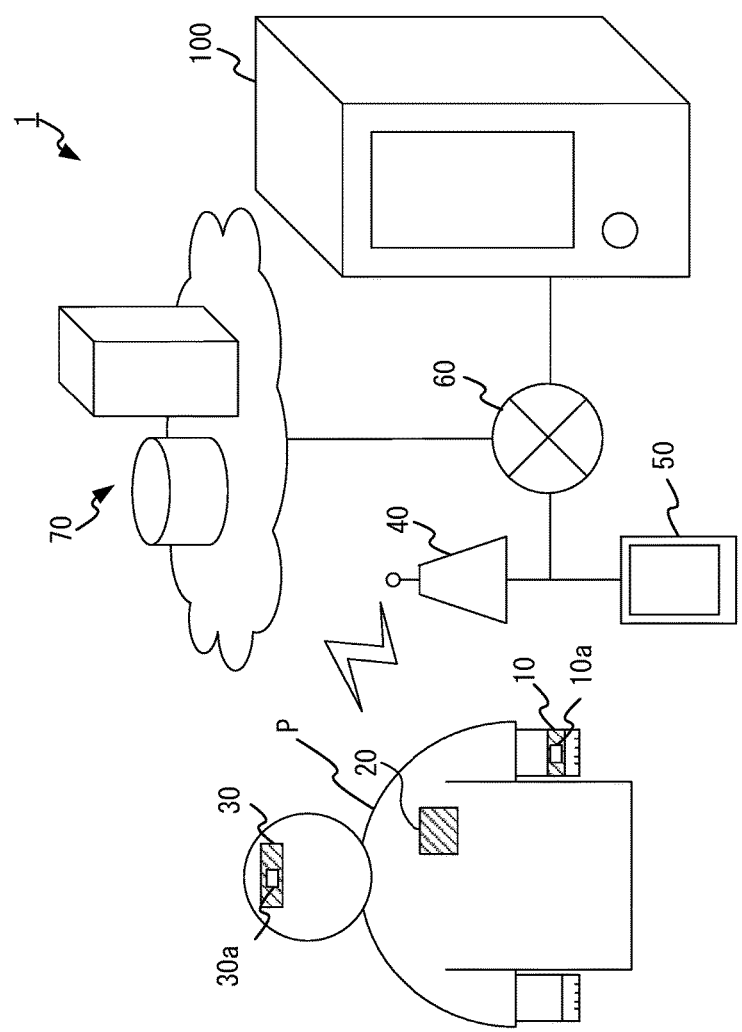
FIG. 1 illustrates a configuration of a biological data processing system 1.

FIG. 1 illustrates a configuration of a biological data processing system 1. The biological data processing system 1 is a medical system that collects biological data of a target patient P using an attachable sensor attached to the target patient P and uses the collected biological data in the treatment or prevention of disease.

In this case, the attachable sensor is a sensor that can be carried around by being attached to a human body, and that wirelessly communicates data with an external device. In addition to a wearable sensor that is attached to a surface of a human body, the attachable sensor includes an implantable sensor that is implanted within a human body. That is, each of a wearable sensor and an implantable sensor is a type of the attachable sensor. The biological data is data that indicates a physiological indicator of a patient, and includes, for example, vital data (data of vital signs including blood pressure, pulse, respiratory rate, and body temperature), brain wave data, and blood glucose data.

As illustrated in FIG. 1, the biological data processing system 1 includes one or more attachable sensors (a wearable sensor 10, an implantable sensor 20, and a wearable sensor 30), an access point 40, an NFC (near field communication) reader 50, a network 60, and a biological data processing apparatus 100. Further, the biological data processing apparatus 100 may be connected to a cloud environment 70 through the network 60 such that the biological data processing apparatus 100 can access the cloud environment 70.

All of the attachable sensors are biological sensors that collect biological data of the target patient P, and are configured to collect biological data and communicate with an external device by power supplied by a battery. Each sensor may obtain one type of biological data or a plurality of types of biological data.

The wearable sensor 10 is a wristband wearable sensor that is worn on a wrist, and collects, for example, body temperature data, pulse data, and blood pressure data. The implantable sensor 20 is an implantable sensor that is implanted within a body, and collects, for example, blood glucose data. The wearable sensor 30 is an eyewear-type wearable sensor or a headset wearable sensor and collects, for example, brain wave data.

The wearable sensor 10 and the wearable sensor 30 include a display 10a and a display 30a, respectively, in order to visually report an abnormality to the target patient P. Instead of or in addition to the display 10a and the display 30a, the wearable sensor 10 and the wearable sensor 30 may include, for example, a speaker, a vibrator, or an LED (light emitting diode) in order to report an abnormality to the target patient P. An abnormality may be reported to the target patient P by sound, vibration, or a light emission using the configurations described above.

Figure 2:
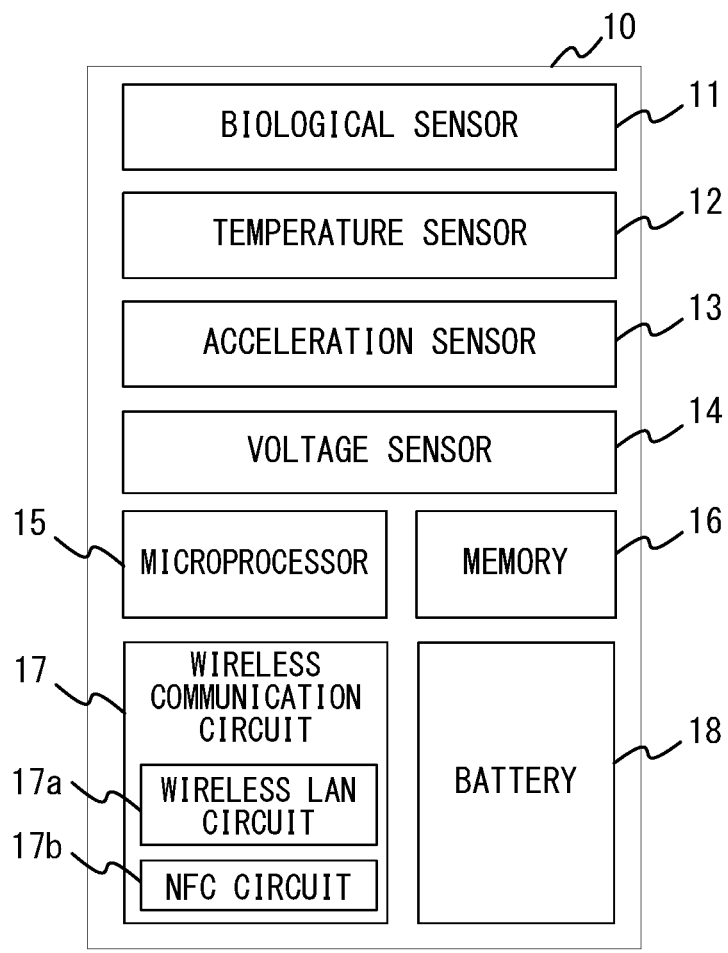
FIG. 2 illustrates a hardware configuration of a wearable sensor 10.

FIG. 2 illustrates a hardware configuration of the wearable sensor 10. The configuration of the wearable sensor 10 is described with reference to FIG. 2 as an example of the attachable sensors. The implantable sensor 20 and the wearable sensor 30 have similar configurations to the configuration of the wearable sensor 10.

As illustrated in FIG. 2, the wearable sensor 10 includes a plurality of sensors (a biological sensor 11, a temperature sensor 12, an acceleration sensor 13, and a voltage sensor 14), a microprocessor 15, a memory 16, a wireless communication circuit 17, and a battery 18. In addition to these components, the wearable sensor 10 may include, for example, a timer that measures a continuous usage time.

The biological sensor 11 is a sensor that measures vital signs including body temperature, pulse, and blood pressure. All of the temperature sensor 12, the acceleration sensor 13, and the voltage sensor 14 measure a state of the wearable sensor 10, wherein the temperature sensor 12 measures a temperature of the wearable sensor 10, the acceleration sensor 13 measures an acceleration imposed on the wearable sensor 10, and the voltage sensor 14 measures a power supply voltage from the battery 18. Using these sensors, data that indicates a state of the wearable sensor 10 (hereinafter referred to as sensor-state data) such as temperature, acceleration, and power supply voltage is collected by the wearable sensor 10. When the wearable sensor 10 includes a timer, a continuous usage time may be further measured. In this case, data indicating a continuous usage time is also included in the sensor-state data. Here, the state of a sensor refers to what may vary over time, and does not include what does not vary over time, such as a physical configuration of the sensor.

Temperature data and acceleration data that are included in the sensor-state data are examples of data that indicates a usage environment of the wearable sensor 10. The sensor-state data may include other data that indicates a usage environment of the wearable sensor 10, such as humidity and an atmospheric pressure. Further, power supply voltage data included in the sensor-state data is an example of data that indicates a state of the battery 18. The sensor-state data may include other data that indicates the state of the battery 18, such as a remaining battery life. Usage time data included in the sensor-state data is an example of data that indicates a deterioration state of the wearable sensor 10. The sensor-state data may include other data that indicates the deterioration state of the wearable sensor 10.

The wireless communication circuit 17 is, for example, an integrated communication chip which corresponds to a plurality of communication methods. Here, an example of including a wireless LAN circuit 17a corresponding to Wi-Fi (Wireless Fidelity)® and a NFC circuit 17b corresponding to an NFC are illustrated, and the wireless communication circuit 17 may further correspond to, for example, BLE (Bluetooth® Low Energy).

In the wearable sensor 10, the wireless communication circuit 17 transmits collected biological data and sensor-state data to the biological data processing apparatus 100. The data transmitted by the wireless communication circuit 17 is transferred, via the access point 40 or the NFC reader 50, to the biological data processing apparatus 100 through the network 60. The wireless communication circuit 17 may transmit data to the access point 40 or the NFC reader 50 through a portable terminal (not illustrated) held by the target patient P, such as a mobile phone or a smartphone. Each of the implantable sensor 20 and the wearable sensor 30 also transmits collected biological data and sensor-state data to the biological data processing apparatus 100 through their own wireless communication circuit.

FIG. 3 illustrates a hardware configuration of the biological data processing apparatus 100. The biological data processing apparatus 100 is an apparatus that processes biological data collected from the target patient P for use in the treatment or prevention of disease.

The biological data processing apparatus 100 includes a processor 101, a memory 102, a storage 103, a network (NW) interface 104, and a portable recording medium driving device 105 into which a portable recording medium 106 is inserted, as illustrated in FIG. 3. These components are connected to one another by a bus 107.

The processor 101 is an electric circuitry such as a CPU (central processing unit), an MPU (micro processing unit), and a DSP (digital signal processor), and executes a program stored in the memory 102 so as to perform programmed processing. The memory 102 includes, for example, a RAM (random access memory), and when the program stored in the memory 102 is executed, a program or data stored in the storage 103 or the portable recording medium 106 is temporarily stored in the RAM.

The storage 103 is, for example, a hard disk and a flash memory, and is a storage device used to primarily record various data and programs. The NW interface 104 is, for example, an NIC (network interface controller) and is hardware that exchanges a signal with an apparatus other than the biological data processing apparatus 100 (such as the wearable sensor 10). The portable recording medium driving device 105 accommodates the portable recording medium 106 such as an optical disk and CompactFlash®. The portable recording medium 106 plays a role in assisting the storage 103. The storage 103 and the portable recording medium 106 are examples of a non-transitory computer-readable medium in which a program is recorded.

The configuration of FIG. 3 is an example of a hardware configuration of the biological data processing apparatus 100, and the biological data processing apparatus 100 is not limited to this configuration. The biological data processing apparatus 100 may be a dedicated apparatus, not a general-purpose apparatus. Instead of or in addition to a processor that executes a program, the biological data processing apparatus 100 may include an electric circuitry such as an ASIC (application specific integrated circuit) or an FPGA (field programmable gate array) so as to process biological data using the electric circuitry.

In the cloud environment 70, various services are provided in the form of SaaS, PaaS, or IaaS. For example, biological data collected by the attachable sensor may be transmitted to the cloud environment 70 in addition to the biological data processing apparatus 100, and the cloud environment 70 may provide, to the biological data processing apparatus 100, a storage service for accumulating, for example, biological data. Further, the cloud environment 70 may provide, to the biological data processing apparatus 100, an analysis service for analyzing the accumulated biological data to make use of it in the prevention or early treatment of disease.

<First Environment>

Figure 7:
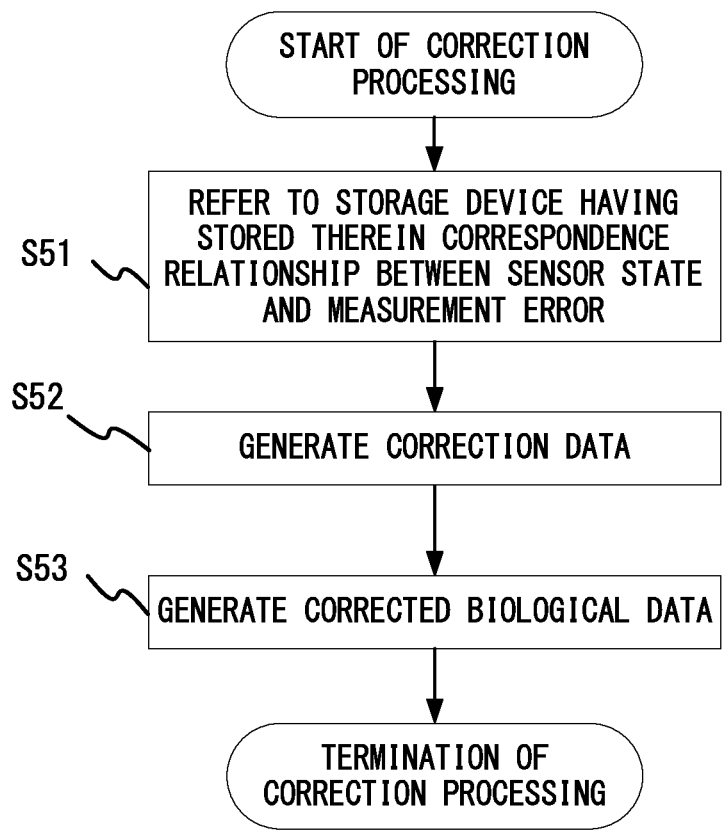
FIG. 7 illustrates an example of a flowchart of correction processing.

FIG. 4 illustrates an example of a flowchart of data processing according to the present embodiment. FIG. 5 illustrates an example of a flowchart of reliability evaluation processing. FIG. 6 illustrates an example of information S1 on an operation permitting condition that is stored in the storage 103. FIG. 7 illustrates an example of a flowchart of correction processing. FIG. 8 illustrates an example of information S2 on a correspondence relationship between a state of a sensor and a measurement error of the sensor that is stored in the storage 103. An example of the data processing performed by the biological data processing apparatus 100 after the biological data processing apparatus 100 obtains biological data and sensor-state data from a biological sensor is described below with reference to FIGS. 4 to 8.

In the biological data processing apparatus 100, the data processing illustrated in FIG. 4 is performed by the processor 101 executing one or more programs stored in the memory 102. Here, an example in which biological data and sensor-state data are regularly transmitted to the biological data processing apparatus 100 from the attachable wearable sensor 10 attached to the target patient P is described.

First, the biological data processing apparatus 100 obtains data transmitted from the wearable sensor 10 (Step S10). Here, the processor 101 obtains, through the NW interface 104, body temperature data that is biological data of the target patient P collected by the wearable sensor 10. The processor 101 further obtains, through the NW interface 104, sensor-state data of the wearable sensor 10 that is collected by the wearable sensor 10. The sensor-state data includes data of temperature, acceleration, and power supply voltage. In Step S10, data (hereinafter referred to as sensor identification data) that identifies a sensor may be obtained in addition to biological data and sensor-state data in order to determine from which of the attachable sensors attached to the target patient P data is obtained.

Next, the biological data processing apparatus 100 performs reliability evaluation processing of evaluating the reliability of biological data obtained from the wearable sensor 10 (Step S20). Here, the reliability of the biological data is evaluated on the basis of an operation permitting condition for the wearable sensor 10 and the sensor-state data of the wearable sensor 10 that is obtained in Step S10.

The reliability evaluation of biological data is to determine whether the reliability of the biological data is high, and more particularly, whether the biological data is reliable. In the reliability evaluation processing in Step S20, the biological data is determined to be reliable when it is estimated that a correct measurement has been performed with respect to a physiological indicator of the target patient P (such as a body temperature), and the biological data is determined to be unreliable when it is estimated that a correct measurement has not been performed with respect to the physiological indicator of the target patient P.

When the reliability evaluation processing is started, the processor 101 refers to the storage 103 that is a storage device having stored therein an operation permitting condition for the wearable sensor 10, as illustrated in FIG. 5 (Step S21). The operation permitting condition for a sensor is a condition under which a normal operation of the sensor is ensured, and is also referred to as a recommended operating condition or an operating condition. The storage 103 has stored therein, for example, information S1 on an operation permitting condition for the wearable sensor 10, as illustrated in FIG. 6. The information S1 indicates that the operation of the wearable sensor 10 is permitted (that is, the wearable sensor 10 operates normally) if the power supply voltage is in the range of 5V±10%. Further, the information S1 indicates that the wearable sensor 10 operates normally if the temperature is in the range of 5° C. to 55° C. and the wearable sensor 10 operates normally if the continuous usage time is within 96 hours. FIG. 6 illustrates the operation permitting condition for the wearable sensor 10, but the information S1 may include information on an operation permitting condition for each sensor (the wearable sensor 10, the implantable sensor 20, and the wearable sensor 30). In this case, the operation permitting condition for a sensor that has been identified by sensor identification data is referred to in Step S21.

After that, the processor 101 that referred to the storage 103 determines whether the sensor-state data obtained in Step S10 satisfies the operation permitting condition (Step S22). Specifically, the processor 101 determines whether power supply voltage data included in the sensor-state data indicates a voltage in the range of 5V±10%, and further determines whether temperature data included in the sensor-state data indicates a temperature in the range of 5° C. to 55° C. When both the power supply voltage data and the temperature data indicate values in the respective ranges described above, the operation permitting condition is determined to be satisfied.

When the operation permitting condition has been determined to be satisfied, the processor 101 determines that the wearable sensor 10 is operating normally and the biological data is reliable (Step S23), and the processor 101 terminates the reliability evaluation processing. On the other hand, when the operation permitting condition has been determined to not be satisfied, the processor 101 estimates that a result of the measurement performed by the wearable sensor 10 is more likely to include an error and determines that the biological data is unreliable (Step S24), and the processor 101 terminates the reliability evaluation processing.

When the biological data has been determined to be unreliable in the reliability evaluation processing (NO in Step S30), the biological data processing apparatus 100 reports an abnormality in the wearable sensor 10 (Step S40). Here, the processor 101 issues a report command that reports the abnormality in the wearable sensor 10 to the target patient P, the report command being issued to the wearable sensor 10 according to the sensor-state data.

The report command may be issued when the determination that the biological data is unreliable has lasted for a certain period of time. Further, the report command may be generated according to sensor-state data, and it may include a message to be displayed on the display 10a. An example of the message is "<WARNING> the temperature of the wearable sensor 10 has increased beyond the operation permitting temperature". The wearable sensor 10 that received the report command performs processing corresponding to that command (for example, processing of displaying a message or the like on the display 10a) so as to report an abnormality in the wearable sensor 10 to the target patient P.

After that, the biological data processing apparatus 100 performs the correction processing on the biological data (Step S50). In this case, the processor 101 corrects the biological data such that the reliability of the biological data is improved.

When the correction processing is started, first, the processor 101 refers to the storage 103 that is a storage device having stored therein a correspondence relationship between a state of the wearable sensor 10 and a measurement error of the wearable sensor 10 (Step S51). The storage 103 has stored therein, for example, information S2 on a correspondence relationship between a state of the wearable sensor 10 and a measurement error of the wearable sensor 10, as illustrated in FIG. 8. The information S2 indicates that a measurement error of $\Delta V \times 10\%$ occurs in body temperature data when the power supply voltage of the battery 18 is not in the range of a permitted voltage (the range of 5V±10%). The information S2 also indicates that when the temperature of the wearable sensor 10 and the continuous usage time of the wearable sensor 10 are not in the respective permitted ranges, measurement errors of $\Delta Tc \times 20\%$ and $-\Delta t \times 3\%$ respectively occur in body temperature data. Here, $\Delta V$, $\Delta Tc$, and $\Delta t$ are a difference between a power supply voltage of the wearable sensor 10 and a permitted power supply voltage, a difference between a temperature of the wearable sensor 10 and an operation permitting temperature, and a difference between a continuous usage time of the wearable sensor 10 and a permitted continuous usage time, respectively.

FIG. 8 illustrates an example in which a measurement error varies linearly with respect to a parameter that indicates a state of a sensor, in order to simplify the descriptions. The correspondence relationship between a state of a sensor and a measurement error of the sensor may be generated on the basis of a measurement result obtained from, for example, an experiment performed in advance. Further, the correspondence relationship may be generated using, for example, a computer simulation, on the basis of, for example, design information on a sensor. Furthermore, the correspondence relationship between a state of a sensor and a measurement error of the sensor may be represented by a function, as illustrated in FIG. 8, or it may be represented as a group of pieces of data stored in a table.

After that, the processor 101 that referred to the storage 103 generates correction data according to the sensor-state data obtained in Step S10 (Step S52). The correction data is data indicating a measurement error that is expected to occur. Specifically, on the basis of the power supply voltage data and the temperature data that are obtained in Step S10 and on the basis of the information S2 stored in the storage 103, the processor 101 calculates a measurement error that occurs in the wearable sensor 10 with respect to body temperature, and generates correction data that indicates the calculated measurement error.

Further, the processor 101 corrects the biological data obtained in Step S10 using the generated correction data, so as to generate corrected biological data obtained by correcting the biological data obtained in Step S10 (Step S53). Specifically, the processor 101 corrects the temperature data obtained in Step S10 by compensating for a measurement error included in the temperature data using the correction data that indicates a measurement error, so as to generate corrected temperature data.

When the corrected biological data has been generated and the correction processing has been completed, the biological data processing apparatus 100 stores the corrected biological data in the storage 103 (Step S60). Here, the processor 101 stores the corrected biological data generated in Step S53 in the storage 103 as evaluated biological data.

On the other hand, when the biological data has been determined to be reliable in the reliability evaluation processing (YES in Step S30), the biological data processing apparatus 100 stores the biological data in the storage 103 (Step S70). Here, the processor 101 stores the biological data obtained in Step S10 in the storage 103 as evaluated biological data.

The evaluated biological data stored in the storage 103 in Step S60 and Step S70 is used in the treatment or prevention of disease of the target patient P. For example, the biological data processing apparatus 100 may analyze accumulated biological data of the target patient P so as to create supplemental information that is used when his/her doctor determines a plan to visit a hospital, a treatment plan, or both for the target patient P.

When the evaluated biological data has been stored, the biological data processing apparatus 100 analyzes the evaluated biological data (Step S80) and determines whether an abnormality has occurred in the target patient P (Step S90). Here, for example, the processor 101 may perform the analysis and determination processing on the basis of newest evaluated biological data stored in the storage 103, or it may perform the analysis and determination processing on the basis of the history of the evaluated biological data stored in the storage 103. A specific method for determining an abnormality is not limited in particular as long as the processor 101 can detect an abnormality in the target patient P on the basis of the evaluated biological data. Any known method may be used for the abnormality determination. For example, the determination may be performed according to whether a state of the target patient P (for example, body temperature) that is indicated by the evaluated biological data is in a predetermined range that represents a range of a normal value.

When the abnormality in the target patient P has not been detected, the data processing illustrated in FIG. 4 is terminated. When the abnormality in the target patient P has been detected on the basis of the evaluated biological data, the biological data processing apparatus 100 reports the abnormality in the target patient P (Step S100), and the data processing illustrated in FIG. 4 is then terminated. In Step S100, the processor 101 issues, to the wearable sensor 10, a report command that reports the abnormality in the target patient P to the target patient P.

The report command may be generated on the basis of the evaluated biological data, and for example, it may include a message to be displayed on the display 10a. An example of the message is "<WARNING> the body temperature is high". A sensor that received the report command performs processing corresponding to the report command so as to report the abnormality in the target patient P.

It is possible to know a state of a sensor by the biological data processing apparatus 100 performing the data processing illustrated in FIG. 4, so biological data output from an attachable sensor used under various circumstances in everyday life can be evaluated properly. In particular, the reliability of biological data can be easily evaluated without performing any complicated operations, by comparing an operation permitting condition determined in advance with a state of a sensor.

Further, an amount of biological data that can be used for diagnosis is increased by performing the correction processing that improves the reliability of biological data with a low reliability. This makes it possible to accumulate more data, so that a diagnosis accuracy improves and treatment or prevention of disease becomes more effective.

Further, it is possible to accurately provide information to a patient by detecting an abnormality in the patient on the basis of biological data with a high reliability (including corrected biological data). Thus, it is expected that the patient has a higher level of confidence in the provided information. Furthermore, it is possible to reduce a risk of overlooking an abnormality in a patient by using corrected biological data generated by correcting biological data with a low reliability to detect an abnormality in the patient.

Moreover, it is possible to urge a patient to change a sensor or to charge a battery by reporting an abnormality in a sensor to the patient. This results in being able to avoid situations where the patient does not notice the abnormality in the sensor and continues to acquire biological data with a low reliability.

In the present embodiment, an example in which an abnormality in a sensor is reported upon detecting the abnormality in the sensor has been described. However, instead of or in addition to reporting the abnormality in the sensor, the biological data processing apparatus 100 may perform the following processing upon detecting the abnormality in the sensor.

For example, if a sensor has a refresh function that recovers a function of the sensor, the biological data processing apparatus 100 may issue, to the sensor, a command (hereinafter referred to as a refresh command) that causes a refresh operation to be performed. This permits the sensor that received the refresh command to perform processing corresponding to the command so that the function of the sensor is recovered, which results in being able to use the sensor longer.

A refresh command is issued not only when an abnormality in a sensor has been detected. A refresh condition that recommends a refresh operation of a sensor may be stored in the storage 103 in advance, and the processor 101 may issue a refresh command that causes the sensor to perform a refresh operation when sensor-state data satisfies the refresh condition stored in the storage 103.

In the present embodiment, an example in which an abnormality in the target patient P is reported upon detecting the abnormality in the target patient P has been described. However, instead of or in addition to reporting the abnormality in the target patient P, the biological data processing apparatus 100 may perform the following processing upon detecting the abnormality in the target patient P.

For example, when only a portion of the sensors attached to the target patient P are used, the biological data processing apparatus 100 may issue a control command that activates other sensors. When only the wearable sensor 10 is running, a control command that activates the implantable sensor 20 and the wearable sensor 30 may be issued to both of the sensors. This makes it possible to obtain more information on the target patient P in an abnormal state, which results in being able to diagnose the condition of the target patient P accurately while saving a battery in a normal state.

Further, for example, the biological data processing apparatus 100 may issue, to a sensor, a control command that changes the communication setting between the biological data processing apparatus 100 and the sensor to a setting in which a communication interval (a transmission interval) for transmitting biological data is shorter. This makes it possible to obtain more information on the target patient P in an abnormal state sooner.

Furthermore, for example, a recommended communication interval in a normal state and a recommended communication interval in an abnormal state may be stored in the storage 103 in advance. The biological data processing apparatus 100 may issue, to a sensor, a control command that changes a communication interval that is set in the sensor such that the communication interval is changed to the recommended communication interval in an abnormal state when an abnormality in the target patient P is detected. The biological data processing apparatus 100 may issue, to the sensor, a control command that changes the communication interval that is set in the sensor such that the communication interval is changed to the recommended communication interval in a normal state when an abnormality in the target patient P is not detected. It is preferable that the recommended communication interval in an abnormal state be shorter than the recommended communication interval in a normal state.

In the present embodiment, an example in which an abnormality in the target patient P is detected on the basis of evaluated biological data has been described, but the abnormality in the target patient P may be detected on the basis of the evaluated biological data and sensor-state data. For example, an activity state of the patient (such as a resting state and a moving state) may be determined from acceleration data included in the sensor-state data, so as to detect an abnormality in the patient while taking into consideration the activity state of the patient. This makes it possible to determine whether the patient is in an abnormal state with a different reference used according to the activity state of the patient, which results in being able to detect an abnormality in the patient more properly.

In the present embodiment, an example in which the biological data processing apparatus 100 that is a standard computer performs the data processing illustrated in FIG. 4 has been described, but a biological data processing apparatus 200 that is a dedicated apparatus as illustrated in FIG. 9 may perform the data processing illustrated in FIG. 4. As illustrated in FIG. 9, the biological data processing apparatus 200 includes a data obtaining circuit 201, a reliability evaluation circuit 202, a correction circuit 203, a target-patient-abnormality detection circuit 204, a command issuance circuit 205, and a storage 206 that is a storage device. The reliability evaluation circuit 202 includes a reference circuit 202a and a determination circuit 202b. The correction circuit 203 includes a reference circuit 203a, a correction data generation circuit 203b, and a corrected biological data generation circuit 203c. The biological data processing apparatus 200 is different from the biological data processing apparatus 100 in that a dedicated circuitry (the data obtaining circuit 201, the reliability evaluation circuit 202, the correction circuit 203, the target-patient-abnormality detection circuit 204, and the command issuance circuit 205) performs various processing that is performed by the processor 101 executing a program, but it is similar to the biological data processing apparatus 100 in regard to the other points. The biological data processing apparatus 200 also permits obtaining of an effect similar to the biological data processing apparatus 100.

Second Embodiment

Figure 11:
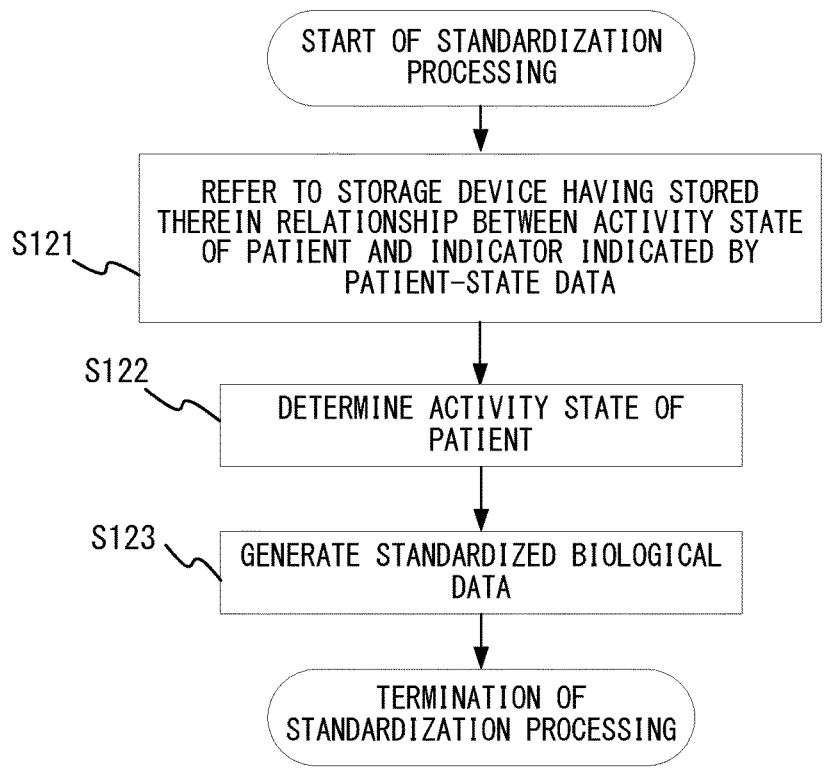
FIG. 11 is an example of a flowchart of standardization processing.

FIG. 10 is an example of a flowchart of data processing according to the present embodiment. FIG. 11 is an example of a flowchart of standardization processing. An example of the data processing performed by the biological data processing apparatus 100 after the biological data processing apparatus 100 obtains biological data and sensor-state data from a biological sensor is described below with reference to FIGS. 10 and 11.

In the biological data processing apparatus 100, the data processing illustrated in FIG. 10 is performed by the processor 101 executing one or more programs stored in the memory 102. Here, an example in which biological data and sensor-state data are regularly transmitted from the attachable wearable sensor 10 to the biological data processing apparatus 100, and biological data and sensor-state data are regularly transmitted from the wearable sensor 30 to the biological data processing apparatus 100 is described, the attachable wearable sensor 10 and the wearable sensor 30 being attached to the target patient P.

First, the biological data processing apparatus 100 obtains data transmitted from the wearable sensor 10 and the wearable sensor 30 (Step S110). Here, the processor 101 obtains pulse data collected by the wearable sensor 10 and brain wave data collected by the wearable sensor 30. The processor 101 further obtains sensor-state data of the wearable sensor 10 and sensor-state data of the wearable sensor 30. The biological data processing apparatus 100 also obtains sensor identification data in addition to the biological data and the sensor-state data.

Next, the biological data processing apparatus 100 performs standardization processing of standardizing the pulse data that is biological data (Step S120). Here, the pulse data that is biological data obtained from the wearable sensor 10 is standardized on the basis of the brain wave data that is biological data obtained from the wearable sensor 30, so as to generate standardized pulse data obtained by standardizing the biological data obtained from the wearable sensor 10 (hereinafter referred to as standardized biological data).

The brain wave data that is a different type of biological data than the pulse data is data that varies according to an activity state of the target patient P (hereinafter referred to as patient-state data), and represents the activity state of the target patient P indirectly. The standardization of biological data means converting biological data obtained from a patient under a certain rule so that a physiological indicator indicated by the biological data can be compared regardless of the activity state of the patient.

When the standardization processing is started, first, the processor 101 refers to the storage 103 that is a storage device having stored therein a correspondence relationship between an activity state of a patient and a physiological indicator indicated by patient-state data, as illustrated in FIG. 11 (Step S121). The correspondence relationship stored in the storage 103 may be a correspondence relationship specific to the target patient P, or it may be a correspondence relationship in a general patient.

Next, the processor 101 that referred to the storage 103 determines the activity state of the target patient P on the basis of the patient-state data obtained in Step S110 (Step S122). Here, the processor 101 determines the activity state of the target patient P on the basis of the brain wave data that is patient-state data and the correspondence relationship stored in the storage 103. The history of brain wave data that includes not only newest brain wave data but also brain wave data obtained in the past may be used to determine the activity state of the target patient P.

After that, the processor 101 standardizes the biological data according to the activity state determined in Step S122, generates standardized biological data (Step S123), and terminates the standardization processing. In Step S123, the processor 101 refers to the storage 103 having stored therein a conversion rule for each activity state, and converts the pulse data that is biological data according to the conversion rule corresponding to the activity state determined in Step S122. It is preferable that the conversion rule differ from one activity state to another, but it is sufficient if at least a conversion rule for one activity state is different from a conversion rule for another activity state.

When the standardized biological data has been generated and the standardization processing has been terminated, the biological data processing apparatus 100 stores the standardized biological data in the storage 103 (Step S130). Here, the biological data processing apparatus 100 may store, in the storage 103, the biological data and the sensor-state data that are obtained in Step S110 along with the standardized biological data.

When the standardized biological data has been stored, the biological data processing apparatus 100 analyzes the standardized biological data (Step S140) and determines whether an abnormality has occurred in the target patient P (Step S150). Here, for example, the processor 101 may perform the analysis and determination processing on the basis of newest standardized biological data stored in the storage 103, or it may perform the analysis and determination processing on the basis of the history of the standardized biological data stored in the storage 103. A specific method for determining an abnormality is not limited in particular as long as the processor 101 can detect an abnormality in the target patient P on the basis of the standardized biological data. Any known method may be used for the abnormality determination. For example, the determination may be performed according to whether a state of the target patient P (for example, pulse) that is indicated by the standardized biological data is in a predetermined range that represents a range of a normal value.

When the abnormality in the target patient P has not been detected, the data processing illustrated in FIG. 10 is terminated. When the abnormality in the target patient P has been detected on the basis of the standardized biological data, the biological data processing apparatus 100 reports the abnormality in the target patient P (Step S160), and the data processing illustrated in FIG. 10 is then terminated. The process of Step S160 is similar to the process of Step S100 in FIG. 4.

It is possible to convert biological data of a patient into data that can be compared regardless of an activity state of the patient by the biological data processing apparatus 100 performing the data processing illustrated in FIG. 10. This makes it easy to properly evaluate biological data obtained from a patient in various activity states. For example, there is a significant difference in pulse between in a resting state and a moving state, but the standardization of pulse data makes it possible to determine an abnormality easily without distinguishing data in a resting state from data in a moving state.

In the present embodiment, an example in which patient-state data is different biological data (brain wave data) than biological data to be standardized (pulse data) has been described, but it is sufficient if the patient-state data varies according to an activity state of a patient, and the patient-state data may be sensor-state data. For example, pulse data may be standardized by obtaining acceleration data of a sensor as patient-state data in Step S110 illustrated in FIG. 10 and by determining the activity state of a patient in Step S120 on the basis of the acceleration data of the sensor. In this case, a correspondence relationship between an activity state of a patient and an acceleration that is a physical indicator indicated by patient-state data is stored in the storage 103. Even if biological data is standardized on the basis of sensor-state data, the biological data will be converted into data that can be compared regardless of an activity state of a patient, which makes it easy to properly evaluate biological data obtained from the patient in various activity states.

Further, in the present embodiment, an example in which an abnormality in the target patient P is reported upon detecting the abnormality in the target patient P has been described. However, instead of or in addition to reporting the abnormality in the target patient P, the biological data processing apparatus 100 may issue, upon detecting the abnormality in the target patient P, a control command that activates other sensors or a control command that changes the setting in a sensor to a setting in which a communication interval for transmitting biological data is shorter.

Figure 12:
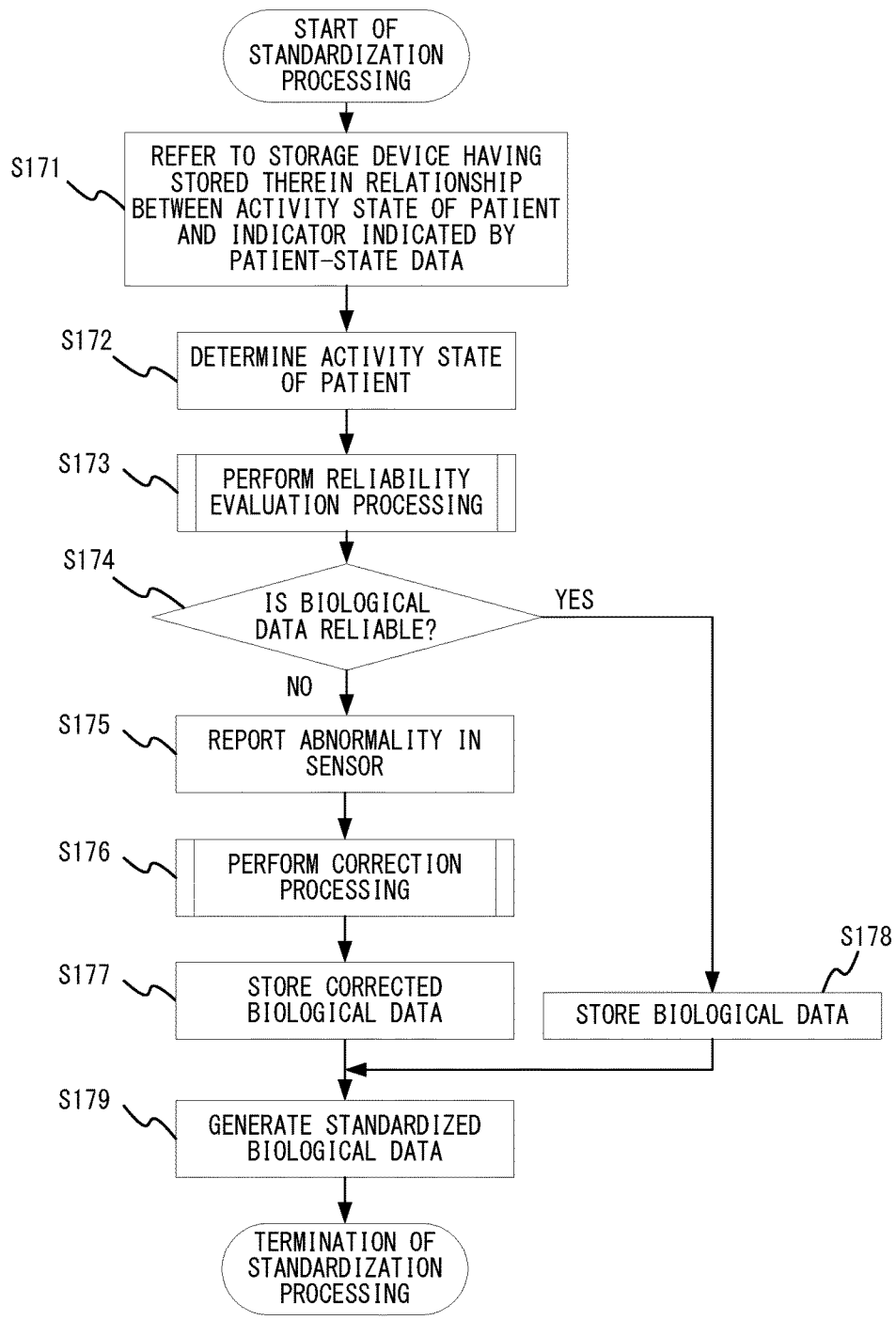
FIG. 12 is another example of the flowchart of standardization processing.

Furthermore, in the present embodiment, the standardization processing illustrated in FIG. 11 has been described as an example of standardization processing, but the biological data processing apparatus 100 may perform standardization processing illustrated in FIG. 12 instead of the standardization processing illustrated in FIG. 11.

When the standardization processing illustrated in FIG. 12 is started, first, the processor 101 refers to the storage 103 that is a storage device having stored therein a correspondence relationship between an activity state of a patient and an indicator indicated by patient-state data (Step S171), and determines the activity state of the patient on the basis of the patient-state data (Step S172). The processes of Step S171 and Step S172 are similar to the processes of Step S121 and Step S122 illustrated in FIG. 11.

After that, the processor 101 performs reliability evaluation processing of evaluating the reliability of biological data to be standardized (in this case, pulse data) (Step S173). Here, the processor 101 evaluates the reliability of the biological data on the basis of the sensor-state data obtained in Step S110 and an operation permitting condition for the sensor. When the biological data has been determined to be unreliable in the reliability evaluation processing (NO in Step S174), the processor 101 reports an abnormality in the wearable sensor 10 (Step S175) and performs correction processing on the biological data (Step S176). The processor 101 stores corrected biological data generated by the correction processing in the storage 103 as evaluated biological data (Step S177). On the other hand, when the biological data has been determined to be reliable in the reliability evaluation processing (YES in Step S174), the processor 101 stores the biological data in the storage 103 as evaluated biological data (Step S178). The processes of Step S173 to Step S178 are similar to the processes of Step S20 to Step S70 in FIG. 4.

When the evaluated biological data has been stored in the storage 103, the processor 101 standardizes the evaluated biological data according to the activity state determined in Step S172, generates standardized biological data (Step S179), and terminates the standardization processing. The process of Step S179 is similar to the process of Step S123 in FIG. 11 except that evaluated biological data is standardized.

Even if the biological data processing apparatus 100 performs the standardization processing illustrated in FIG. 12 instead of the standardization processing illustrated in FIG. 11 when it performs data processing, the biological data will be converted into data that can be compared regardless of an activity state of a patient. This makes it easy to properly evaluate biological data obtained from a patient in various activity states.

Further, it is possible to obtain an effect similar to the data processing according to the first embodiment by the biological data processing apparatus 100 performing the standardization processing illustrated in FIG. 12 instead of the standardization processing illustrated in FIG. 11 when it performs data processing. Specifically, an amount of biological data that can be used for diagnosis is increased because the correction processing is performed. This makes it possible to accumulate more data, so that a diagnosis accuracy improves and treatment or prevention of disease becomes more effective. Further, it is possible to accurately provide information to a patient because an abnormality in the patient is detected on the basis of biological data with a high reliability (including corrected biological data). Furthermore, it is possible to reduce a risk of overlooking an abnormality in a patient by using corrected biological data to detect an abnormality in the patient. Moreover, it is possible to urge a patient to change a sensor or to charge a battery because an abnormality in a sensor is reported to the patient. This results in being able to avoid situations where the patient does not notice the abnormality in the sensor and continues to acquire biological data with a low reliability.

In FIG. 12, an example in which the reliability of biological data to be standardized is evaluated and a correction is performed when the reliability is low has been described, but the reliability may also be evaluated with respect to biological data that is patient-state data in addition to the biological data to be standardized, and the correction may be performed when the reliability is low. This makes the reliability of the patient-state data higher, which results in being able to standardize the biological data more accurately.

Further, in FIG. 12, an example in which an abnormality in a sensor is reported upon detecting the abnormality in the sensor has been described. However, instead of or in addition to reporting the abnormality in the sensor, the biological data processing apparatus 100 may issue a refresh command upon detecting the abnormality in the sensor, as in the first embodiment.

Figure 13:
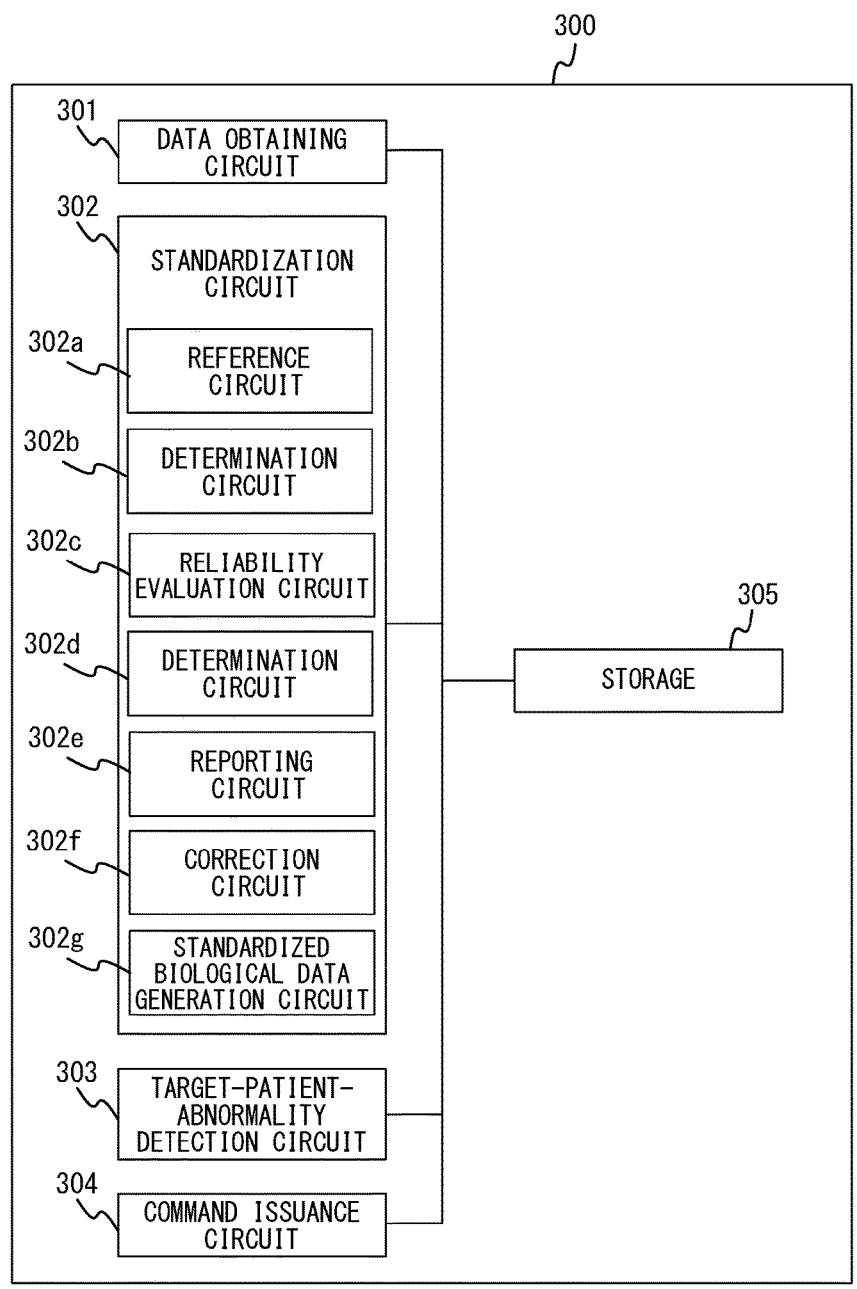
FIG. 13 illustrates a hardware configuration of a biological data processing apparatus 300 according to another modification.

In the present embodiment, an example in which the biological data processing apparatus 100 that is a standard computer performs the data processing illustrated in FIG. 10 has been described, but a biological data processing apparatus 300 that is a dedicated apparatus as illustrated in FIG. 13 may perform the data processing illustrated in FIG. 10. As illustrated in FIG. 13, the biological data processing apparatus 300 includes a data obtaining circuit 301, a standardization circuit 302, a target-patient-abnormality detection circuit 303, a command issuance circuit 304, and a storage 305 that is a storage device. The standardization circuit 302 includes a reference circuit 302a, a determination circuit 302b, a reliability evaluation circuit 302c, a determination circuit 302d, a reporting circuit 302e, a correction circuit 302f, and a standardized biological data generation circuit 302g. The biological data processing apparatus 300 is different from the biological data processing apparatus 100 in that a dedicated circuitry (the data obtaining circuit 301, the standardization circuit 302, the target-patient-abnormality detection circuit 303, and the command issuance circuit 304) performs various processing that is performed by the processor 101 executing a program, but it is similar to the biological data processing apparatus 100 in regard to the other points. The biological data processing apparatus 300 also permits obtaining of an effect similar to the biological data processing apparatus 100.

Third Embodiment

Figure 14:
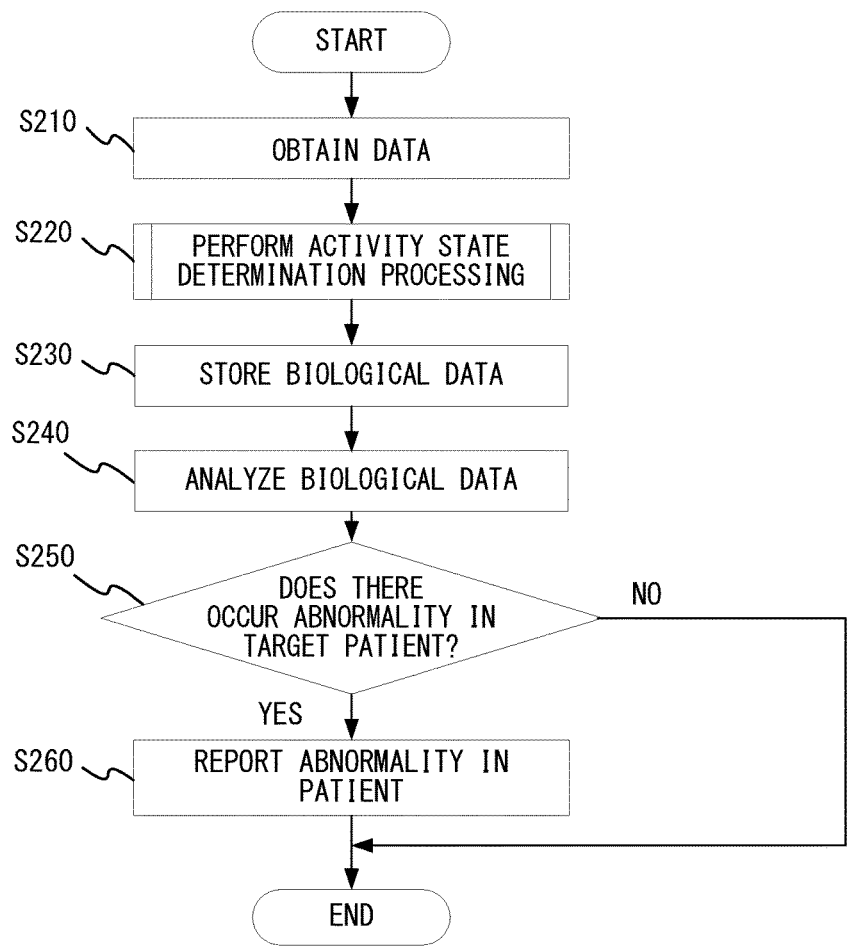
FIG. 14 illustrates an example of a flowchart of data processing according to a third embodiment.
Figure 15:
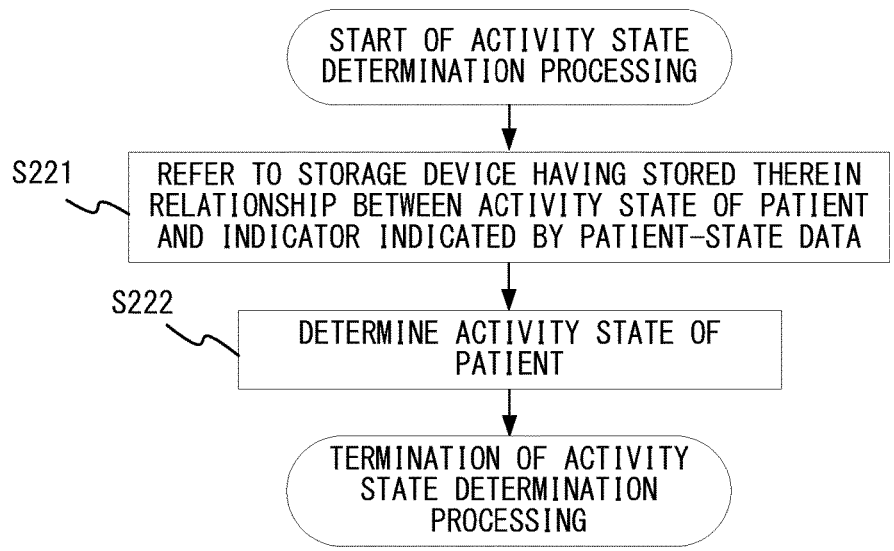
FIG. 15 illustrates an example of a flowchart of activity state determination processing.

FIG. 14 illustrates an example of a flowchart of data processing according to the present embodiment. FIG. 15 illustrates an example of a flowchart of activity state determination processing. An example of the data processing performed by the biological data processing apparatus 100 after the biological data processing apparatus 100 obtains biological data and sensor-state data from a biological sensor is described below with reference to FIGS. 14 and 15.

In the biological data processing apparatus 100, the data processing illustrated in FIG. 14 is performed by the processor 101 executing one or more programs stored in the memory 102. Here, as in the second embodiment, an example in which biological data and sensor-state data are regularly transmitted from the attachable wearable sensor 10 to the biological data processing apparatus 100, and biological data and sensor-state data are regularly transmitted from the wearable sensor 30 to the biological data processing apparatus 100 is described, the attachable wearable sensor 10 and the attachable wearable sensor 30 being attached to the target patient P.

First, the biological data processing apparatus 100 obtains data transmitted from the wearable sensor 10 and the wearable sensor 30 (Step S210). Here, the processor 101 obtains pulse data collected by the wearable sensor 10 and brain wave data collected by the wearable sensor 30. The processor 101 further obtains sensor-state data of the wearable sensor 10 and sensor-state data of the wearable sensor 30. The biological data processing apparatus 100 also obtains sensor identification data in addition to the biological data and the sensor-state data.

Next, the biological data processing apparatus 100 performs activity state determination processing of determining an activity state of the target patient P. (Step S220). Here, the activity state of the target patient P to which the wearable sensor 30 is attached is determined on the basis of the brain wave data that is biological data obtained from the wearable sensor 30. The brain wave data that is a different type of biological data than the pulse data is patient-state data that varies according to an activity state of the target patient P, and represents the activity of the target patient P indirectly.

When the activity state determination processing is started, first, the processor 101 refers to the storage 103 that is a storage device having stored therein a correspondence relationship between an activity state of a patient and a physiological indicator indicated by patient-state data, as illustrated in FIG. 15 (Step S221). After that, the processor 101 determines the activity state of the target patient P on the basis of the patient-state data obtained in S210 (Step S222), and terminates the activity state determination processing.

The processes of Step S221 and Step S222 are similar to the processes of Step S121 and Step S122 in FIG. 11.

When the activity state determination processing has been terminated, the biological data processing apparatus 100 stores the biological data in the storage 103 (Step S230). Here, the biological data processing apparatus 100 may store, in the storage 103, the sensor-state data obtained in Step S210 along with the biological data obtained in Step S210 (pulse data and brain wave data).

When the biological data has been stored, the biological data processing apparatus 100 analyzes the biological data (Step S240) and determines whether an abnormality has occurred in the target patient P (Step S250). Here, the processor 101 detects the abnormality in the target patient P on the basis of the activity state determined in Step S220 and the pulse data that is biological data obtained in Step S210. The biological data (pulse data) used for the abnormality detection may be newest biological data stored in the storage 103, or it may be the history of the biological data stored in the storage 103.

Specifically, the processor 101 may detect an abnormality by performing, for example, the following processing. First, the processor 101 refers to the storage 103 that is a storage having stored therein a correspondence relationship between an activity state of the target patient P and a range of a normal value for a physiological indicator (in this case, pulse) indicated by biological data. Then, the processor 101 detects an abnormality in the target patient P on the basis of the activity state determined in Step S220, the pulse data obtained in Step S210, and the correspondence relationship stored in the storage 103. In more detail, on the basis of the correspondence relationship stored in the storage 103, the processor 101 determines a range of a normal value for a pulse that corresponds to the activity state determined in Step S220. After that, when the pulse indicated by the pulse data obtained in Step S210 is not in the determined range of a normal value, the processor 101 determines that the abnormality has occurred.

When the abnormality in the target patient P has not been detected, the data processing illustrated in FIG. 14 is terminated. When the abnormality in the target patient P has been detected, the biological data processing apparatus 100 reports the abnormality in the target patient P (Step S260), and the data processing illustrated in FIG. 14 is then terminated. The process of Step S260 is similar to the process of Step S100 in FIG. 4.

It is possible to determine, with a different reference used according to the activity state of a patient, whether the patient is in an abnormal state by the biological data processing apparatus 100 performing the data processing illustrated in FIG. 14. This results in being able to evaluate biological data properly so as to detect an abnormality in the patient more properly. For example, there is a significant difference in pulse between a resting state and a moving state, but the determination with a different reference used makes it possible to detect the abnormality in the patient properly.

In the present embodiment, an example in which patient-state data is different biological data (brain wave data) than biological data (pulse data) that is compared to a range of a normal value has been described, but as in the second embodiment, it is sufficient if the patient-state data varies according to an activity state of a patient, and the patient-state data may be, for example, sensor-state data such as acceleration data.

Further, in the present embodiment, an example in which an abnormality in the target patient P is reported upon detecting the abnormality in the target patient P has been described. However, instead of or in addition to reporting the abnormality in the target patient P, the biological data processing apparatus 100 may issue, upon detecting the abnormality in the target patient P, a control command that activates other sensors or a control command that changes the setting in a sensor to a setting in which a communication interval for transmitting biological data is shorter.

Figure 16:
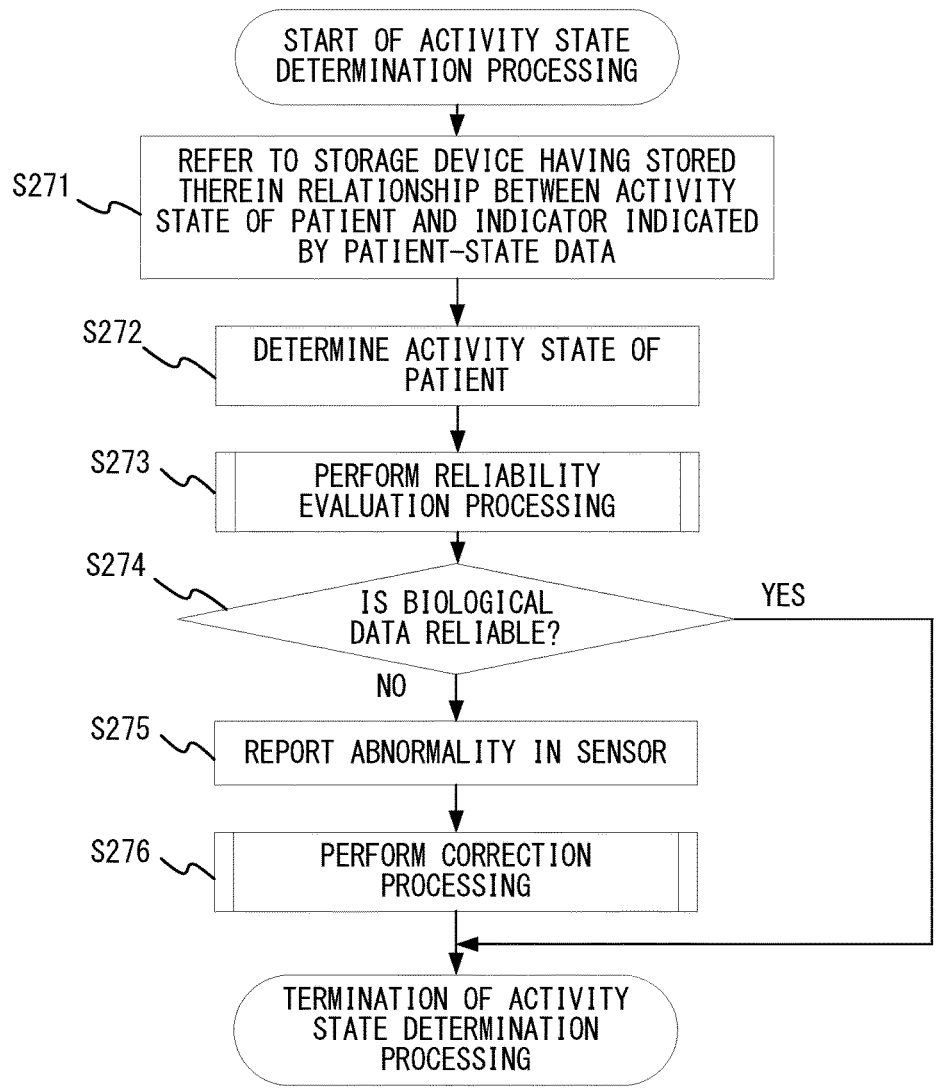
FIG. 16 illustrates another example of the flowchart of activity state determination processing.

Furthermore, in the present embodiment, the activity state determination processing illustrated in FIG. 15 has been described as an example of activity state determination processing, but the biological data processing apparatus 100 may perform activity state determination processing illustrated in FIG. 16 instead of the activity state determination processing illustrated in FIG. 15.

When the activity state determination processing illustrated in FIG. 16 is started, first, the processor 101 refers to the storage 103 that is a storage device having stored therein a correspondence relationship between an activity state of a patient and an indicator indicated by patient-state data (Step S271), and determines the activity state of the patient on the basis of the patient-state data (Step S272). The processes of Step S271 and Step S272 are similar to the processes of Step S221 and Step S222 illustrated in FIG. 15.

After that, the processor 101 performs reliability evaluation processing of evaluating the reliability of biological data (in this case, pulse data) (Step S273). Here, the processor 101 evaluates the reliability of the biological data on the basis of the sensor-state data obtained in Step S210 and an operation permitting condition for the sensor. When the biological data has been determined to be reliable in the reliability evaluation processing (YES in Step S274), the processor 101 terminates the activity state determination processing. On the other hand, when the biological data has been determined to be unreliable in the reliability evaluation processing (NO in Step S274), the processor 101 reports an abnormality in the wearable sensor 10 (Step S275), performs correction processing on the biological data (Step S276), and terminates the activity state determination processing. The processes of Step S273 to Step S276 are similar to the processes of Step S20 to Step S50 in FIG. 4.

Even if the biological data processing apparatus 100 performs the activity state determination processing illustrated in FIG. 16 instead of the activity state determination processing illustrated in FIG. 15 when it performs data processing, it will be possible to determine an activity state of a patient. This makes it easy to properly evaluate biological data obtained from a patient in various activity states, so as to properly detect an abnormality in the patient.

Further, it is possible to obtain an effect similar to the data processing according to the first embodiment by the biological data processing apparatus 100 performing the activity state determination processing illustrated in FIG. 16 instead of the activity state determination illustrated in FIG. 15 when it performs data processing.

In FIG. 16, an example in which the reliability of biological data (in this case, pulse data) that is compared to a range of a normal value is evaluated and a correction is performed when the reliability is low has been described, but the reliability may also be evaluated with respect to biological data (in this case, brain wave data) that is patient-state data, and the correction may be performed when the reliability is low. This makes the reliability of the patient-state data higher, which results in being able to determine an activity state of a patient more properly.

Further, in FIG. 16, an example in which an abnormality in a sensor is reported upon detecting the abnormality in the sensor has been described. However, instead of or in addition to reporting the abnormality in the sensor, the biological data processing apparatus 100 may issue a refresh command upon detecting the abnormality in the sensor, as in the first embodiment.

In the present embodiment, an example in which the biological data processing apparatus 100 that is a standard computer performs the data processing illustrated in FIG. 14 has been described, but a biological data processing apparatus 400 that is a dedicated apparatus as illustrated in FIG. 17 may perform the data processing illustrated in FIG. 14. As illustrated in FIG. 17, the biological data processing apparatus 400 includes a data obtaining circuit 401, an activity state determination circuit 402, a target-patient-abnormality detection circuit 403, a command issuance circuit 404, and a storage 405 that is a storage device. The activity state determination circuit 402 includes a reference circuit 402a and a determination circuit 402b. The biological data processing apparatus 400 is different from the biological data processing apparatus 100 in that a dedicated circuitry (the data obtaining circuit 401, the activity state determination circuit 402, the target-patient-abnormality detection circuit 403, and the command issuance circuit 404) performs various processing that is performed by the processor 101 executing a program, but it is similar to the biological data processing apparatus 100 in regard to the other points. The biological data processing apparatus 400 also permits obtaining of an effect similar to the biological data processing apparatus 100.

Fourth Embodiment

Figure 19:
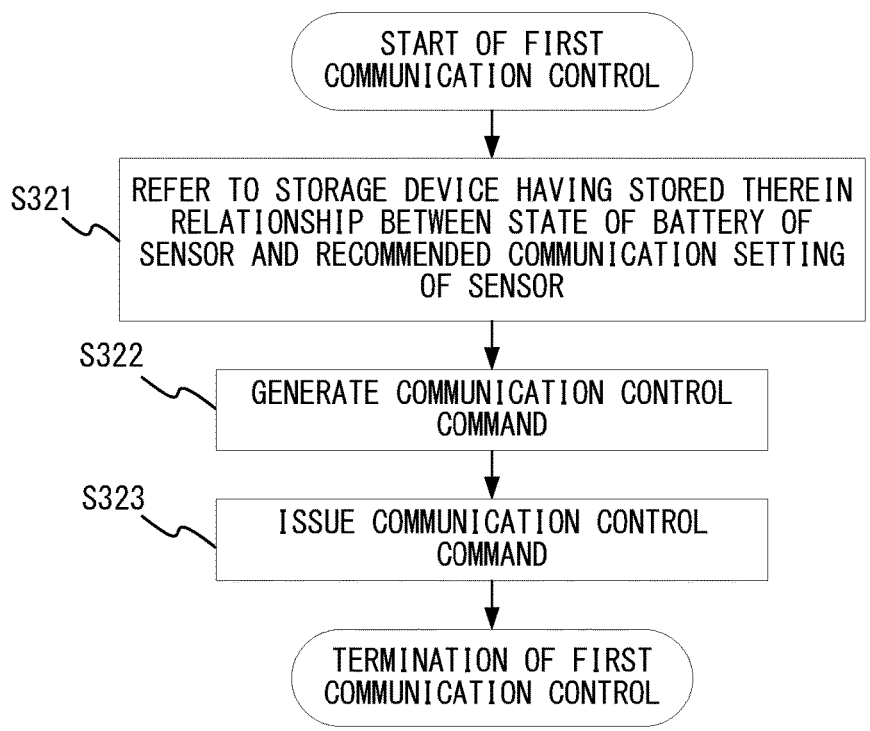
FIG. 19 illustrates an example of a flowchart of first communication control processing.
Figure 20:
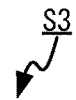
FIG. 20 illustrates an example of information S3 on a recommended communication setting stored in the storage 103.
Figure 21:
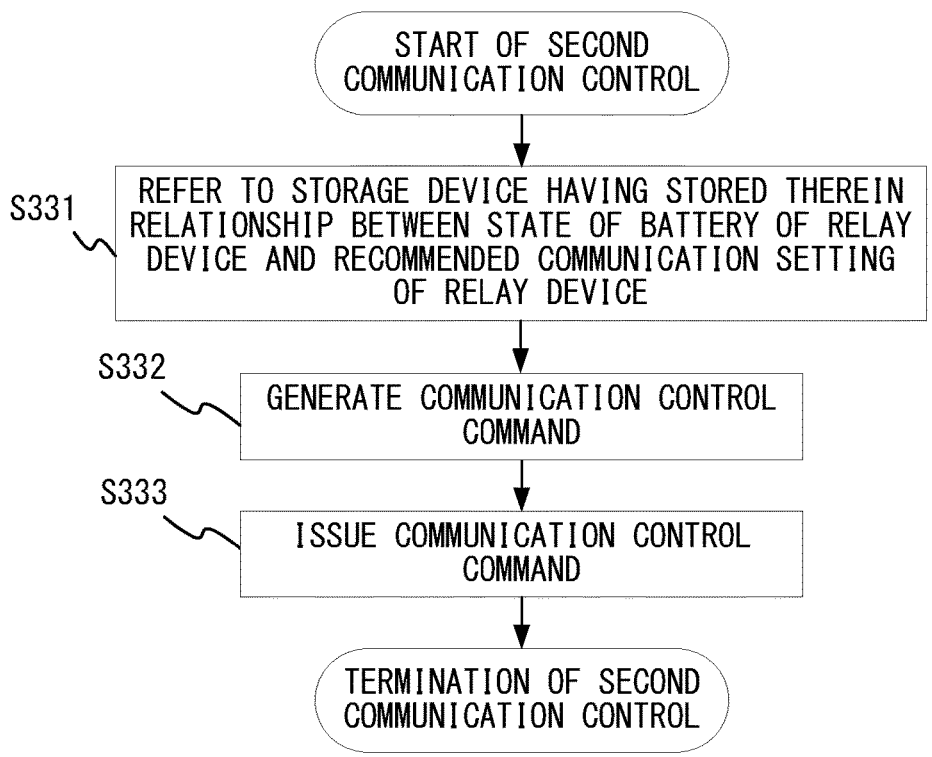
FIG. 21 illustrates an example of a flowchart of second communication control processing.

FIG. 18 illustrates an example of a flowchart of data processing according to the present embodiment. FIG. 19 illustrates an example of a flowchart of first communication control processing. FIG. 20 illustrates an example of information S3 on a recommended communication setting stored in the storage 103. FIG. 21 illustrates an example of a flowchart of second communication control processing. An example of data processing performed by the biological data processing apparatus 100 after the biological data processing apparatus 100 obtains biological data and battery data from a biological sensor and obtains battery data from a relay device is described below with reference to FIGS. 18 to 21. The battery data is data that indicates a battery state, and includes, for example, power supply voltage data and remaining-battery-life data.

In the biological data processing apparatus 100, the data processing illustrated in FIG. 18 is performed by the processor 101 executing one or more programs stored in the memory 102. Here, an example in which biological data and battery data are regularly transmitted from the attachable wearable sensor 10 to the biological data processing apparatus 100, and battery data is regularly transmitted from a relay device (not illustrated) possessed by the target patient P to the biological data processing apparatus 100 is described.

First, the biological data processing apparatus 100 obtains data transmitted from the wearable sensor 10 and the relay device (Step S310). Here, the processor 101 obtains pulse data that is biological data collected by the wearable sensor 10 and supply voltage data that is battery data of the battery 18 of the wearable sensor 10. Further, the processor 101 obtains power supply voltage data that is battery data of a battery of the relay device possessed by the target patient P. In the following descriptions, the battery data of the battery 18 is referred to as first battery data, and the battery data of the relay device is referred to as second battery data.

Next, the biological data processing apparatus 100 performs first communication control processing of controlling a communication between the wearable sensor 10 and the biological data processing apparatus 100 (Step S320). Here, on the basis of the first battery data obtained from the wearable sensor 10, the biological data processing apparatus 100 issues a communication control command that changes the communication setting made in the wearable sensor 10 to a setting corresponding to the first battery data.

When the first communication control processing is started, the processor 101 refers to the storage 103 that is a storage device having stored therein a correspondence relationship between a state of the battery 18 and a recommended communication setting of the wearable sensor 10, as illustrated in FIG. 19 (Step S321). The storage 103 has stored therein, for example, information S3 on a correspondence relationship between a state of the battery 18 and a recommended communication setting of the wearable sensor 10, as illustrated in FIG. 20. The information S3 indicates that a recommended communication method is Wi-Fi and a recommended communication interval is 60 s when the power supply voltage indicating the state of the battery 18 is 4.5V or more, that a recommended communication method is Wi-Fi and a recommended communication interval is 300 s when the power supply voltage is included between 4V and less than 4.5V, and that a recommended communication method is NFC when the power supply voltage is less than 4V.

In FIG. 20, an example of a recommended communication setting of the wearable sensor 10 has been described, but the information S3 may include information on a recommended communication setting for each sensor (the wearable sensor 10, the implantable sensor 20, and the wearable sensor 30). In this case, in Step S321, a recommended communication setting of a sensor identified by sensor identification data is referred to. It is sufficient if the recommended communication setting includes at least one of a recommended time interval and a recommended communication method used by a sensor or a relay device to transmit biological data.

After that, the processor 101 that referred to the storage 103 generates a communication control command on the basis of the first battery data obtained in Step S310 and the correspondence relationship referred to in Step 321 (Step S322). Further, the processor 101 issues the communication control command generated in Step S322 to the wearable sensor 10 (Step S323), and terminates the first communication control processing. The wearable sensor 10 that received the communication control command performs processing corresponding to that command, so as to change the communication setting of the wearable sensor 10 to a recommended communication setting corresponding to the battery state of the battery 18. Specifically, at least one of a communication interval and a communication method is changed.

Further, the biological data processing apparatus 100 performs second communication control processing of controlling a communication between the relay device and the biological data processing apparatus 100 (Step S330). Here, on the basis of the second battery data obtained from the relay device, the biological data processing apparatus 100 issues a communication control command that changes the communication setting made in the relay device to a setting corresponding to the second battery data.

When the second communication control processing is started, the processor 101 refers to the storage 103 that is a storage device having stored therein a correspondence relationship between a state of the relay device and a recommended communication setting of the relay device, as illustrated in FIG. 21 (Step S331). After that, the processor 101 generates a communication control command on the basis of the second battery data obtained in Step S310 and the correspondence relationship referred to in Step S331 (Step S332). Further, the processor 101 issues the communication control command generated in Step S332 to the relay device (Step S333), and terminates the second communication control processing. The relay device that received the communication control command performs processing corresponding to that command, so as to change the communication setting of the relay device to a recommended communication setting corresponding to the battery state of the battery of the relay device. Specifically, at least one of a communication interval and a communication method is changed.

When the second communication control processing is terminated, the processor 101 reports the state of the battery 18 (Step S340). Here, the processor 101 issues, to the wearable sensor 10, a report command (hereinafter referred to as a first report command) that reports a state of the battery 18 to the target patient P. The first report command may be issued under a specific condition (such as when a remaining battery life falls below a threshold).

The first report command may be generated according to the state of the battery 18, or it may include a message to be displayed on the display 10a. An example of the message is "the battery of the sensor is running low". The wearable sensor 10 that received the first report command performs processing corresponding to the command (such as processing of displaying a message or the like on the display 10a), so as to report the state of the battery 18 to the target patient P.

Next, the processor 101 predicts battery exhaustion in the wearable sensor 10 (Step S350), and reports a result of the battery exhaustion prediction (Step S360). Here, the processor 101 predicts the occurrence of battery exhaustion in the wearable sensor 10 on the basis of the first battery data. Specifically, for example, the processor 101 may predict the time elapsed before the battery dies not only on the basis of newest first battery data but also on the basis of, for example, the history of the first battery data and the battery capacity of the battery 18. After that, the processor 101 issues, to the wearable sensor 10, a report command (hereinafter referred to as a second report command) that reports information based on the prediction.

The second report command may include a message to be displayed on the display 10a. An example of the message is "the battery of the sensor will die in about an hour". The wearable sensor 10 that received the second report command performs processing corresponding to the command (such as processing of displaying a message or the like on the display 10a), so as to report a result of the battery exhaustion prediction to the target patient P.

When the report processing has been terminated, the biological data processing apparatus 100 stores the biological data in the storage 103 (Step S370). Here, the biological data processing apparatus 100 may store, in the storage 103, the battery data obtained in Step S310 along with the biological data obtained in Step S310 (pulse data).

When the biological data has been stored, the biological data processing apparatus 100 analyzes the biological data (Step S380) and determines whether an abnormality has occurred in the target patient P (Step S390). The processes of Step S380 and S390 are similar to the processes of Step S80 and Step S90 in FIG. 4

When the abnormality in the target patient P has not been detected, the data processing illustrated in FIG. 18 is terminated. When the abnormality in the target patient P has been detected, the biological data processing apparatus 100 reports the abnormality in the target patient P (Step S400), and the data processing illustrated in FIG. 18 is then terminated. In Step S400, the processor 101 issues, to the wearable sensor 10, a report command that reports the abnormality in the target patient P to the target patient P. The process of Step S400 is similar to the process of Step S100 in FIG. 4.

The communication setting is changed according to the state of a battery of a sensor by the biological data processing apparatus 100 performing the data processing illustrated in FIG. 18. This adjusts power consumption in the sensor according to the state of the battery, which results in being able to delay the timing of battery exhaustion. Further, the state of a battery and information on a battery exhaustion prediction are reported to a patient, so it becomes possible to urge the patient to take an action such as a change or a charge of the battery. This makes it possible to avoid the occurrence of battery exhaustion, which may prevent biological data from being transmitted, or which may interrupt the collection of biological data.

In the present embodiment, an example in which the biological data processing apparatus 100 that is a standard computer performs the data processing illustrated in FIG. 18 has been described, but a biological data processing apparatus 500 that is a dedicated apparatus as illustrated in FIG. 22 may perform the data processing illustrated in FIG. 18. As illustrated in FIG. 22, the biological data processing apparatus 500 includes a data obtaining circuit 501, a battery exhaustion prediction circuit 502, a target-patient-abnormality detection circuit 503, a command issuance circuit 504, and a storage 505 that is a storage device. The biological data processing apparatus 500 is different from the biological data processing apparatus 100 in that a dedicated circuitry (the data obtaining circuit 501, the battery exhaustion prediction circuit 502, the target-patient-abnormality detection circuit 503, and the command issuance circuit 504) performs various processing that is performed by the processor 101 executing a program, but it is similar to the biological data processing apparatus 100 in regard to the other points. The biological data processing apparatus 500 also permits obtaining of an effect similar to the biological data processing apparatus 100.

Fifth Embodiment

Figure 23:
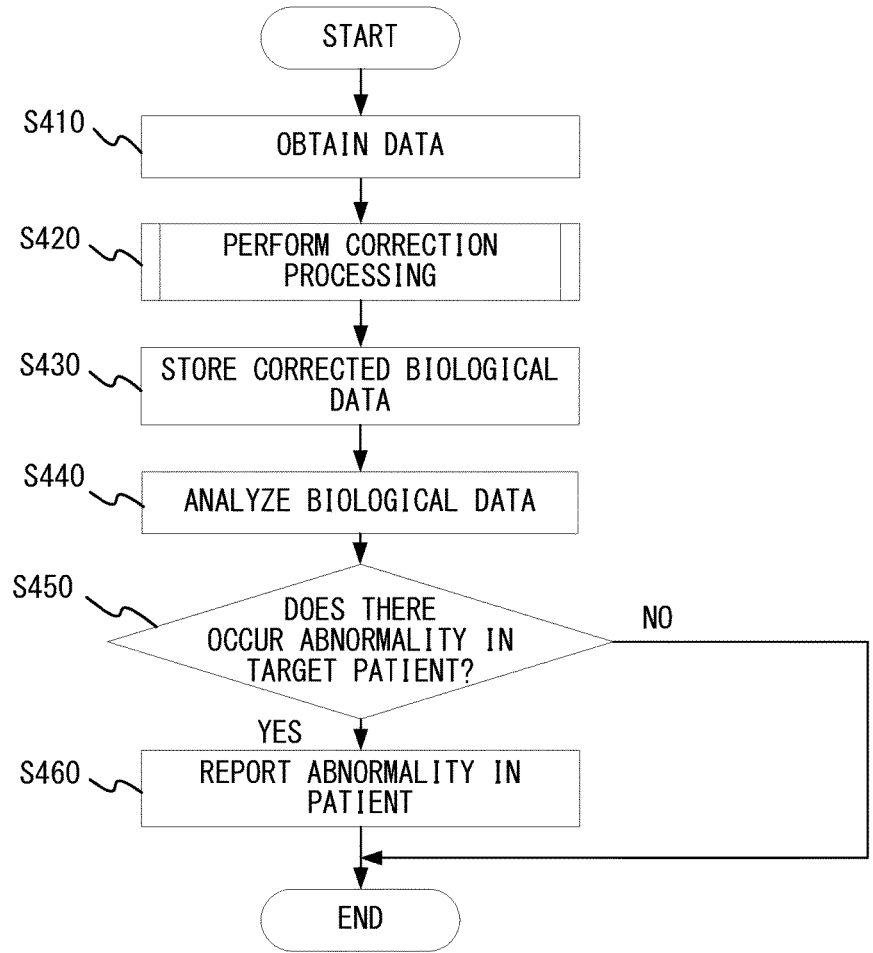
FIG. 23 illustrates an example of a flowchart of data processing according to a fifth embodiment.

FIG. 23 illustrates an example of a flowchart of data processing according to the present embodiment. An example of data processing performed by the biological data processing apparatus 100 after the biological data processing apparatus 100 obtains biological data and battery data from a biological sensor is described below with reference to FIG. 23.

In the biological data processing apparatus 100, the data processing illustrated in FIG. 23 is performed by the processor 101 executing one or more programs stored in the memory 102. Here, an example in which biological data and battery data are regularly transmitted from the attachable wearable sensor 10 attached to the target patient P to the biological data processing apparatus 100 is described.

First, the biological data processing apparatus 100 obtains data transmitted from the wearable sensor 10 (Step S410). Here, the processor 101 obtains pulse data that is biological data collected by the wearable sensor 10 and battery data of the battery 18 (such as power supply voltage data).

Next, the biological data processing apparatus 100 performs the correction processing on the biological data (Step S420). In this case, the processor 101 corrects the pulse data that is biological data on the basis of the battery data such that the reliability of the pulse data is improved, and generates corrected pulse data that is corrected biological data. The process of Step S420 is similar to the correction processing illustrated in FIG. 7 except that biological data is corrected on the basis of battery data. In other words, the processor 101 refers to the storage 103 having stored therein a correspondence relationship between a state of a battery and a measurement error of the wearable sensor 10 (such as the information S2 in FIG. 8, and generates correction data corresponding to the battery data. After that, the processor 101 corrects the pulse data using the correction data, so as to generate corrected pulse data.

When the correction processing has been completed, the biological data processing apparatus 100 stores the corrected biological data in the storage 103 (Step S430). Here, the biological data processing apparatus 100 may store, in the storage 103, the battery data obtained in Step S410 along with the corrected pulse data generated in Step S420.

When the corrected biological data has been stored, the biological data processing apparatus 100 analyzes the corrected biological data (Step S440) and determines whether an abnormality has occurred in the target patient P (Step S450). The processes of Step S440 and Step S450 are similar to the processes of Step S80 and Step S90 in FIG. 4. In other words, the processor 101 detects the abnormality in the target patient P on the basis of the corrected biological data.

When the abnormality in the target patient P has not been detected, the data processing illustrated in FIG. 23 is terminated. When the abnormality in the target patient P has been detected, the biological data processing apparatus 100 reports the abnormality in the target patient P (Step S460), and the data processing illustrated in FIG. 23 is then terminated. In Step S460, the processor 101 issues, to the wearable sensor 10, a report command that reports the abnormality in the target patient P to the target patient P. The process of Step S460 is similar to the process of Step S100 in FIG. 4.

It is possible to correct a measurement error due to the state of a battery in a sensor by the biological data processing apparatus 100 performing the data processing illustrated in FIG. 23. Thus, biological data can be evaluated properly. Further, it becomes possible to accumulate more data and an amount of biological data that can be used for diagnosis is increased, so that a diagnosis accuracy improves and treatment or prevention of disease becomes more effective.

Further, it is possible to accurately provide information to a patient by detecting an abnormality in the patient on the basis of biological data with a high reliability. Thus, it is expected that the patient will have a higher level of confidence in the provided information.

In the present embodiment, an example in which an abnormality in the target patient P is reported upon detecting the abnormality in the target patient P has been described. However, instead of or in addition to reporting the abnormality in the target patient P, the biological data processing apparatus 100 may perform the following processing upon detecting the abnormality in the target patient P.

For example, when only a portion of the sensors attached to the target patient P are used, the biological data processing apparatus 100 may issue a control command that activates other sensors. Further, for example, the biological data processing apparatus 100 may issue, to a sensor, a control command that changes the communication setting between the biological data processing apparatus 100 and the sensor to a setting in which a communication interval for transmitting biological data is shorter. Furthermore, for example, a recommended communication interval in a normal state and a recommended communication interval in an abnormal state may be stored in the storage 103 in advance. The biological data processing apparatus 100 may issue, to a sensor, a control command that changes a communication interval that is set in the sensor such that the communication interval is changed to the recommended communication interval in an abnormal state when an abnormality in the target patient P is detected and such that the communication interval is changed to the recommended communication interval in a normal state when an abnormality in the target patient P is not detected.

Also in the present embodiment, the communication setting may be changed according to battery data, as in the fourth embodiment. In other words, the processor 101 may issue a communication control command that changes the communication setting made in a sensor to a setting corresponding to the battery data.

In the present embodiment, an example in which obtained biological data is corrected regardless of the reliability of the biological data has been described, but the biological data may be corrected when the reliability of the biological data is low. In other words, the biological data may be corrected when battery data does not satisfy the operation permitting condition. In this case, the flow of the processing is similar to that of FIG. 4.

Figure 24:
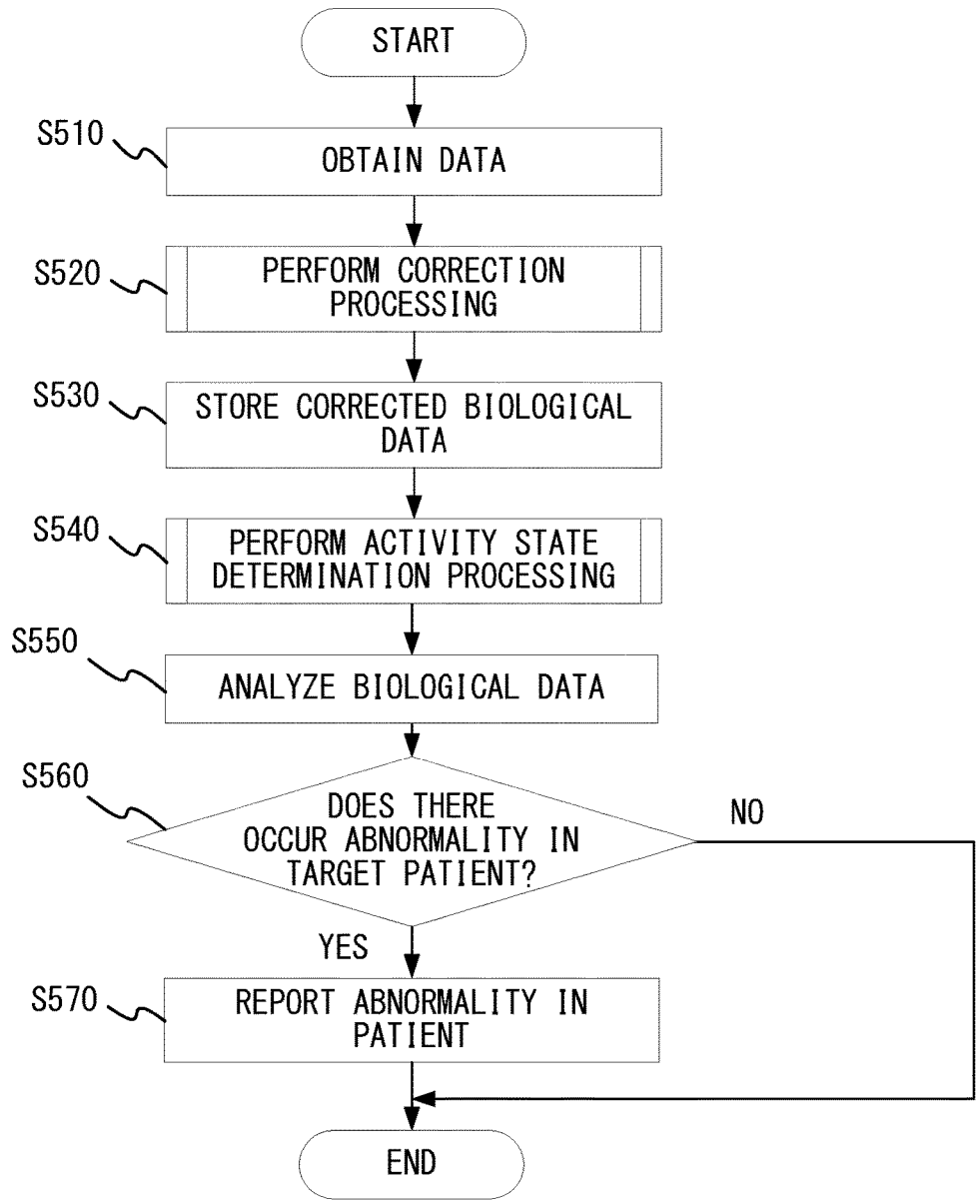
FIG. 24 is a modification of the flowchart of the data processing illustrated in FIG. 23.

In the present embodiment, an example in which an abnormality in the target patient P is detected without considering the activity state of the target patient P has been described, but the data processing illustrated in FIG. 24 may be performed so as to detect the abnormality in the target patient P while taking into consideration the activity state of the target patient P.

The data processing illustrated in FIG. 24 is different from the data processing illustrated in FIG. 23 in that patient-state data is additionally obtained in Step S510, the activity state is determined on the basis of the patient-state data in Step S540, and an abnormality in the target patient P is detected on the basis of the activity state and the biological data in Step S550. The activity state determination processing in Step S540 and the analysis processing in Step S550 are similar to the process of Step S220 and the process of Step S240 in FIG. 14.

In the present embodiment, an example in which an abnormality in the target patient P is detected without standardizing biological data has been described, but the data processing illustrated in FIG. 25 may be performed so as to detect an abnormality in the target patient P on the basis of standardized biological data.

The data processing illustrated in FIG. 25 is different from the data processing illustrated in FIG. 23 in that biological data is standardized in Step S630, standardized biological data is stored in Step S640, and an abnormality in the target patient P is detected on the basis of the standardized biological data in Step S650. The standardization processing in Step S630, the storing processing in Step S640, and the analysis processing in Step S650 are similar to the process of Step S120 (a processing series illustrated in FIG. 11 or 12), the process of Step S130, and the process of Step S140 in FIG. 10.

Figure 26:
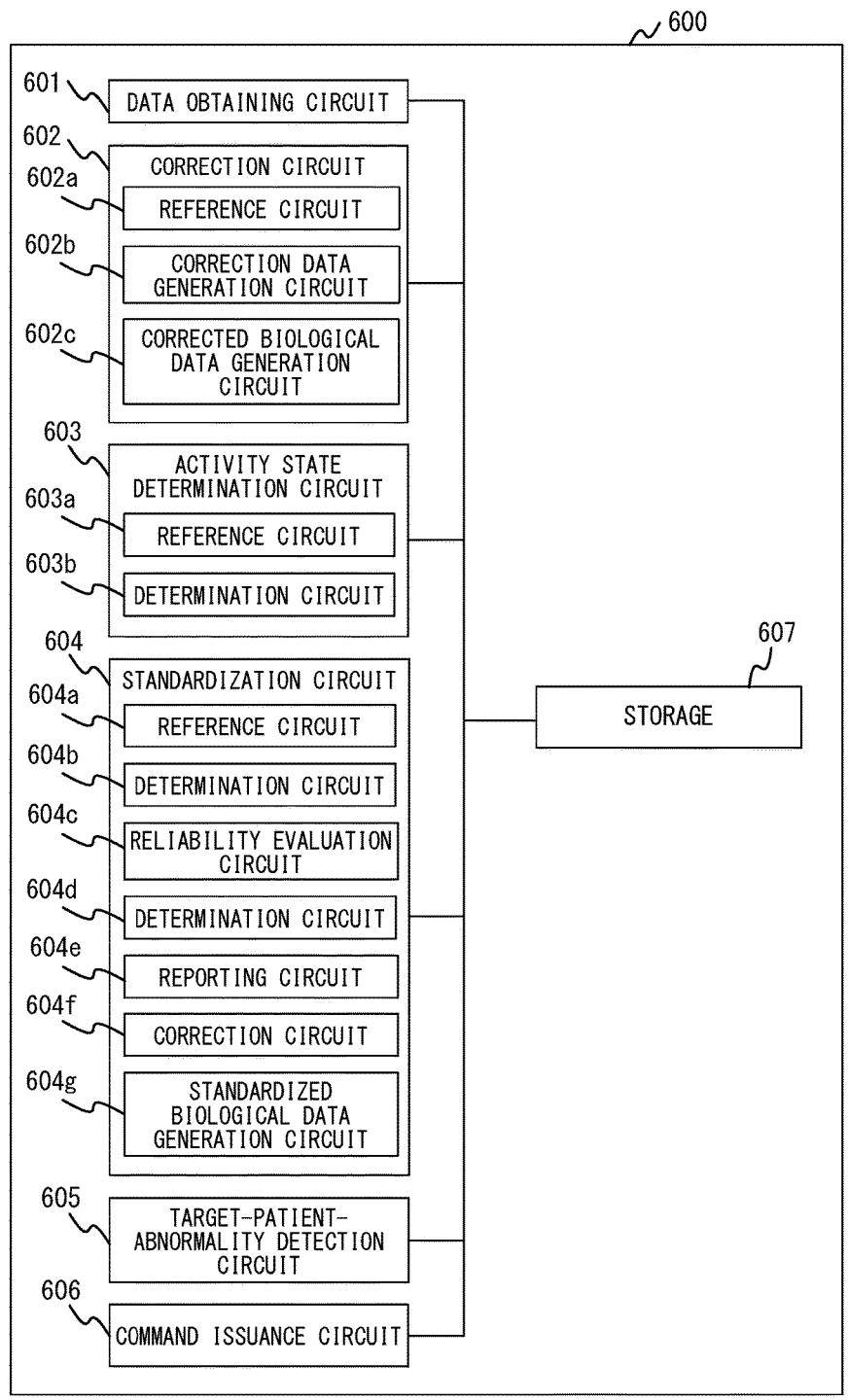
FIG. 26 illustrates a hardware configuration of a biological data processing apparatus 600 according to yet another modification.

In the present embodiment, an example in which the biological data processing apparatus 100 that is a standard computer performs the data processing illustrated in FIG. 23, 24, or 25 has been described, but a biological data processing apparatus 600 that is a dedicated apparatus as illustrated in FIG. 26 may perform the data processing illustrated in FIG. 23, 24, or 25. As illustrated in FIG. 26, the biological data processing apparatus 600 includes a data obtaining circuit 601, a correction circuit 602, an activity state determination circuit 603, a standardization circuit 604, a target-patient-abnormality detection circuit 605, a command issuance circuit 606, and a storage 607 that is a storage device. The correction circuit 602 includes a reference circuit 602a, correction data generation circuit 602b, and a corrected biological data generation circuit 602c. The activity state determination circuit 603 includes a reference circuit 603a and a determination circuit 603b. The standardization circuit 604 includes a reference circuit 604a, a determination circuit 604b, a reliability evaluation circuit 604c, a determination circuit 604d, a reporting circuit 604e, a correction circuit 604f, and a standardized biological data generation circuit 604g. The biological data processing apparatus 600 is different from the biological data processing apparatus 100 in that a dedicated circuitry (the data obtaining circuit 601, the correction circuit 602, the activity state determination circuit 603, the standardization circuit 604, the target-patient-abnormality detection circuit 605, and the command issuance circuit 606) performs various processing that is performed by the processor 101 executing a program, but it is similar to the biological data processing apparatus 100 in regard to the other points. The biological data processing apparatus 600 also permits obtaining of an effect similar to the biological data processing apparatus 100.

The embodiments described above are just examples to facilitate understanding of the present invention, and the embodiment of the present invention is not limited to these examples. Various modifications and alterations may be made to an apparatus, a computer-readable medium, and a method without departing from the recitation of the claims.

What is claimed is:

1. An apparatus for detecting a biological data of a target patient from an attachable sensor attached to the target patient, the apparatus comprising:
   a circuit; and
   a storage that stores therein a first correspondence relationship between a state of a battery included in the sensor and a measurement error of the sensor, wherein
   the circuit is configured to
      obtain the biological data and battery data indicating the state of the battery, the obtained biological data and the obtained battery data being collected by the sensor, and
      generate corrected biological data by correcting the biological data according to the battery data, wherein
   the generating of the corrected biological data includes
      generating correction data that depends on the battery data by referring to the storage that stores the first correspondence relationship, and
      generating the corrected biological data by correcting the biological data using the correction data.

2. The apparatus according to claim 1, wherein
the storage further stores therein an operation permitting condition of the sensor,
the generating of the correction data includes
   referring to the storage that stores therein the operation permitting condition, and
   generating correction data that depends on the battery data by referring to the storage that stores therein the first correspondence relationship when the battery data does not satisfy the operation permission condition.

3. The apparatus according to claim 1, wherein
the circuit is further configured to detect an abnormality in the target patient according to the corrected biological data.

4. The apparatus according to claim 2, wherein
the circuit is further configured to detect an abnormality in the target patient according to the corrected biological data.

5. The apparatus according to claim 1, wherein
the circuit is further configured to
   obtain patient-state data of the target patient that is collected by the sensor,
   determine an activity state of the target patient according to the patient-state data, and
   detect an abnormality in the target patient according to the corrected biological data and the determined activity state of the target patient.

6. The apparatus according to claim 2, wherein
the circuit is further configured to
   obtain patient-state data of the target patient that is collected by the sensor,
   determine an activity state of the target patient according to the patient-state data, and
   detect an abnormality in the target patient according to the corrected biological data and the determined activity state of the target patient.

7. The apparatus according to claim 1, wherein
the circuit is further configured to
   obtain patient-state data of the target patient that is collected by the sensor,
   determine an activity state of the target patient according to the patient-state data, and
   generate standardized biological data by standardizing the corrected biological data in accordance with the determined activity state of the target patient, and
   detect an abnormality in the target patient according to the standardized biological data.

8. The apparatus according to claim 2, wherein
the circuit is further configured to
   obtain patient-state data of the target patient that is collected by the sensor,
   determine an activity state of the target patient according to the patient-state data, and
   generate standardized biological data by standardizing the corrected biological data in accordance with the determined activity state of the target patient, and
   detect an abnormality in the target patient according to the standardized biological data.

9. The apparatus according to claim 1, wherein
the circuit is further configured to
   when an abnormality in the target patient is detected, issue a command for reporting the abnormality in the target patient to the target patient.

10. The apparatus according to claim 2, wherein
the circuit is further configured to
   when an abnormality in the target patient is detected, issue a command for reporting the abnormality in the target patient to the target patient.

11. The apparatus according to claim 3, wherein
the circuit is further configured to
when an abnormality in the target patient is detected, issue a command for reporting the abnormality in the target patient to the target patient.

12. The apparatus according to claim 1, wherein
the circuit is further configured to
when an abnormality in the target patient is detected, issue a control command to change a communication setting between the apparatus and the sensor to a setting in which a communication interval for transmitting the biological data is shorter.

13. The apparatus according to claim 2, wherein
the circuit is further configured to
when an abnormality in the target patient is detected, issue a control command to change a communication setting between the apparatus and the sensor to a setting in which a communication interval for transmitting the biological data is shorter.

14. The apparatus according to of claim 1, wherein
the circuit is further configured to
when an abnormality in the target patient is detected, issue a control command to activate a second sensor that is different from a first sensor that is the sensor attached to the target patient.

15. The apparatus according to of claim 2, wherein
the circuit is further configured to
when an abnormality in the target patient is detected, issue a control command to activate a second sensor that is different from a first sensor that is the sensor attached to the target patient.

16. The apparatus according to claim 1, wherein
the circuit is further configured to
issue a communication control command to change the communication setting that is set for the sensor to a setting that depends on the battery data.

17. The apparatus according to claim 2, wherein
the circuit is further configured to
issue a communication control command to change the communication setting that is set for the sensor to a setting that depends on the battery data.

18. A non-transitory computer-readable medium having recorded therein a program for causing a computer to perform a process for detecting a biological data of a target patient from an attachable sensor attached to the target patient, the process comprising:
obtaining the biological data and battery data indicating a state of a battery included in the sensor, the obtained biological data and the obtained battery data being collected by the sensor; and
generating corrected biological data by correcting the biological data according to the battery data, wherein
the generating of the corrected biological data includes
generating correction data that depends on the battery data by referring to a storage that stores a first correspondence relationship between the state of the battery and a measurement error of the sensor, and
generating the corrected biological data by correcting the biological data using the correction data.

19. A method for detecting a biological data of a target patient from an attachable sensor attached to the target patient, the method comprising:
obtaining the biological data and battery data indicating a state of a battery included in the sensor, the obtained biological data and the obtained battery data being collected by the sensor; and
generating corrected biological data by correcting the biological data according to the battery data, wherein
the generating of the corrected biological data includes
generating correction data that depends on the battery data by referring to a storage that stores a first correspondence relationship between the state of the battery and a measurement error of the sensor, and
generating the corrected biological data by correcting the biological data using the correction data.

* * * * *